US008372680B2

(12) United States Patent
Chen

(10) Patent No.: US 8,372,680 B2
(45) Date of Patent: Feb. 12, 2013

(54) THREE-DIMENSIONAL, ULTRASONIC TRANSDUCER ARRAYS, METHODS OF MAKING ULTRASONIC TRANSDUCER ARRAYS, AND DEVICES INCLUDING ULTRASONIC TRANSDUCER ARRAYS

(75) Inventor: Jingkuang Chen, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 818 days.

(21) Appl. No.: 11/685,199

(22) Filed: Mar. 12, 2007

(65) Prior Publication Data

US 2007/0264732 A1 Nov. 15, 2007

Related U.S. Application Data

(60) Provisional application No. 60/780,828, filed on Mar. 10, 2006, provisional application No. 60/804,018, filed on Jun. 6, 2006, provisional application No. 60/836,162, filed on Aug. 7, 2006.

(51) Int. Cl.
*H01L 21/00* (2006.01)
*H04R 25/00* (2006.01)
(52) U.S. Cl. .......... 438/62; 257/415; 257/416; 257/367; 257/246
(58) Field of Classification Search .................. 257/415, 257/416, 367, 246
See application file for complete search history.

(56) References Cited

U.S. PATENT DOCUMENTS

| 4,783,821 | A  | * | 11/1988 | Muller et al. ............... 381/173 |
| 5,160,870 | A  | * | 11/1992 | Carson et al. .............. 310/339 |
| 5,870,351 | A  | * | 2/1999 | Ladabaum et al. ......... 367/163 |
| 6,430,109 | B1 | * | 8/2002 | Khuri-Yakub et al. ..... 367/181 |
| 7,114,397 | B2 | * | 10/2006 | Fortin et al. ................ 73/756 |
| 7,530,952 | B2 | * | 5/2009 | Huang et al. .............. 600/459 |
| 2005/0183733 | A1 | * | 8/2005 | Kawano et al. ............. 128/899 |
| 2008/0194053 | A1 | * | 8/2008 | Huang ........................ 438/53 |

FOREIGN PATENT DOCUMENTS

JP 08078515 A * 9/1994

* cited by examiner

*Primary Examiner* — Julio J Maldonado
*Assistant Examiner* — Mohammad Choudhry
(74) *Attorney, Agent, or Firm* — Schwegman, Lundberg & Woessner, P.A.

(57) ABSTRACT

Medical imaging devices may comprise an array of ultrasonic transducer elements. Each transducer element may comprise a substrate having a doped surface creating a highly conducting surface layer, a layer of thermal oxide on the substrate, a layer of silicon nitride on the layer of thermal oxide, a layer of silicon dioxide on the layer of silicon nitride, and a layer of conducting thin film on the layer of silicon dioxide. The layers of silicon dioxide and thermal oxide may sandwich the layer of silicon nitride, and the layer of conducting thin film may be separated from the layer of silicon nitride by the layer of silicon dioxide.

17 Claims, 23 Drawing Sheets

FIG. D

THREE-DIMENSIONAL, ULTRASONIC TRANSDUCER ARRAYS, METHODS OF MAKING ULTRASONIC TRANSDUCER ARRAYS, AND DEVICES INCLUDING ULTRASONIC TRANSDUCER ARRAYS

CROSS-REFERENCE TO RELATED APPLICATIONS

This application claims the benefit of priority of U.S. provisional application No. 60/780,828, entitled "Wireless Multi-directional Capsule Endoscopes," filed on Mar. 10, 2006, U.S. provisional patent application No. 60/804,018, entitled "Multi-directional Ultrasonic Imager Array," filed on Jun. 6, 2006, and U.S. provisional application No. 60/836,162, entitled "Monolithic Three Dimensional Ultrasonic Transducer Array with Through-Wafer Electrical Interconnects," filed on Aug. 7, 2006, the contents of all of which are incorporated herein by reference in their entirety.

TECHNICAL FIELD

The present invention is directed generally to transducer arrays, methods of making transducer arrays, and devices including transducer arrays. More particularly, the present invention is directed to three-dimensional, ultrasonic transducer arrays, methods of making ultrasonic transducer arrays, and medical devices including ultrasonic transducer arrays.

BACKGROUND

Some conventional ultrasonic transducers, either piezoelectric or Capacitive Micromachined Ultrasonic Transducer (CMUT), are built on a bulky (e.g., greater than 500 μm thick) piece of silicon or other substrate and arranged in one-dimensional or two-dimensional arrays for medical imaging. Many of these conventional ultrasonic imagers are able to look in only one direction.

One exception to the above-described conventional transducers is the piezoelectric side-viewing imager used in Intravascular Ultrasonic Imagers (IVUS). This device includes a one-dimensional array of piezoelectric transducer mounted on the surface of a catheter to form a cylindrical array that can scan 360°. However, this piezoelectric transducer is limited to providing only two-dimensional images rather than real-time three-dimensional images as needed by many diagnostic processes.

Additionally, due to the difficulty of mounting multiple pieces of transducers on the front and the side of a catheter platform, commercial IVUS are typically equipped with either a side-looking imager or a front-looking imager, but not both.

Thus, it may be desirable to provide a miniature, monolithic ultrasonic imager having multi-direction-looking capabilities and the ability to provide real-time three-dimensional images.

Currently there is a commercially available ingestible capsule endoscope, called Pillcam, which uses a miniature CMOS camera hiding inside a plastic capsule to shoot color photographs of the gastrointestinal (GI) tract. As a minimally invasive device, Pillcam can be swallowed like a vitamin pill and can provide useful image information for diagnosing stomach or small-intestine disorders. Although Pillcam causes far less discomfort for the patient and can reach a much further extent than is capable by the traditional tube endoscope, it has three basic constraints. First, it can only see the surface of the gastrointestinal tract and can not see into the tissue. This limits its capability in determining the extent of a tumor or abnormality in the digestive organs. Secondly, Pillcam cannot shoot images of the colon or rectum because of blockage of stool. As a result, a colonscopy is need for diagnosing the disorders in the colon or rectum and the process is very discomfortable. Thirdly, Pillcam has only one camera and can only look at one direction when it (randomly) travels through the digestive tract. This could result in missing of critical images for a diagnosing process.

It may be desirable to provide an ingestible capsule endoscope that can provide imaging in more than one direction and/or an endoscope that can provide ultrasonic and visible light imaging.

SUMMARY OF THE INVENTION

In various aspects, the present disclosure is directed to medical imaging devices that may comprise an array of ultrasonic transducer elements. Each transducer element may comprise a substrate having a doped surface creating a highly conducting surface layer, a layer of thermal oxide on the substrate, a layer of silicon nitride on the layer of thermal oxide, a layer of silicon dioxide on the layer of silicon nitride, and a layer of conducting thin film on the layer of silicon dioxide. The layers of silicon dioxide and thermal oxide may sandwich the layer of silicon nitride, and the layer of conducting thin film may be separated from the layer of silicon nitride by the layer of silicon dioxide.

In some aspects, methods of fabricating an array of ultrasonic transducers for a medical imaging device may comprise doping a surface of a substrate to create a highly conducting surface layer, growing a layer of thermal oxide on the highly conducting surface layer of the substrate, depositing a layer of silicon nitride on the layer of thermal oxide, depositing a layer of silicon dioxide on the layer of silicon nitride, and depositing a layer of conducting thin film on the layer of silicon dioxide. The layers of silicon dioxide and thermal oxide may sandwich the layer of silicon nitride, and the layer of conducting thin film may be separated from the layer of silicon nitride by the layer of silicon dioxide In various aspects, the present disclosure is directed to medical imaging devices comprising an array of ultrasonic transducer elements. Each transducer element may comprise a substrate having a doped surface creating a highly conducting surface layer, a plurality of sandwiched dielectric layers, a first layer of conducting thin film on the dielectric layers, and a second layer of conducting thin film. The first layer of conducting thin film and the substrate may sandwich the dielectric layers. The second layer of conducting thin film may have a portion in contact with the first layer of conducting thin film and a portion separated from the first layer of conducting thin film, said second layer having at least one hole therethrough. A vacuum cavity may be between the first and second layers of conducting thin film. Each element may include a silicon nitride film on the second layer of conducting thin film, with the silicon nitride film extending through the hole in the second layer and into the vacuum cavity so as to prevent portions of the second layer from collapsing the vacuum cavity and contacting the first layer.

In some aspects, methods of fabricating a medical imaging device may comprise doping a surface of a substrate to create a highly conducting surface layer, growing a layer of thermal oxide on the highly conducting surface layer of the substrate, depositing at least one layer of dielectric film on the layer of thermal oxide, and depositing a first layer of conducting thin film on the at least one layer of dielectric film. The first layer of conducting thin film and the substrate may sandwich the dielectric layers. The methods may include depositing and patterning a sacrificial oxide on the first layer and depositing a second layer of conducting thin film on the patterned sacrificial oxide such that the second layer may have a portion in contact with the first layer of conducting thin film and a portion separated from the first layer of conducting thin film. The methods may include creating at least one hole through the second layer, wherein the hole extends into the sacrificial oxide. The methods may include depositing a silicon nitride film on the second layer of conducting thin film, wherein the silicon nitride film extends through the hole in the second layer and into the hole in the sacrificial oxide. The methods may include removing the sacrificial oxide to create a vacuum cavity between the first and second layers of conducting thin film.

In various aspects, the present disclosure is directed to medical devices configured to be swallowed by a patient. The devices may include a plurality of micro-machined transducers. Each transducer may be configured to send and receive ultrasonic waves in a direction different from that of other transducers.

In various aspects, wireless capsule endoscopes may comprise a plurality of micro-machined transducers. Each transducer may be configured to send and receive ultrasonic waves in a direction different from that of other transducers.

In some aspects, the present disclosure is directed to methods of imaging a digestive tract of a patient. The methods may comprise introducing a capsule endoscope into the digestive tract, wherein the capsule contains a plurality of micro-machined transducers configured to send and receive ultrasonic waves in a direction different from that of other transducers. The method may also include generating ultrasonic waves with said plurality of transducers, receiving ultrasonic waves being directed toward said transducers by portions of the digestive tract, and generating ultrasonic images based on the received waves.

DETAILED DESCRIPTION

Figure 1:
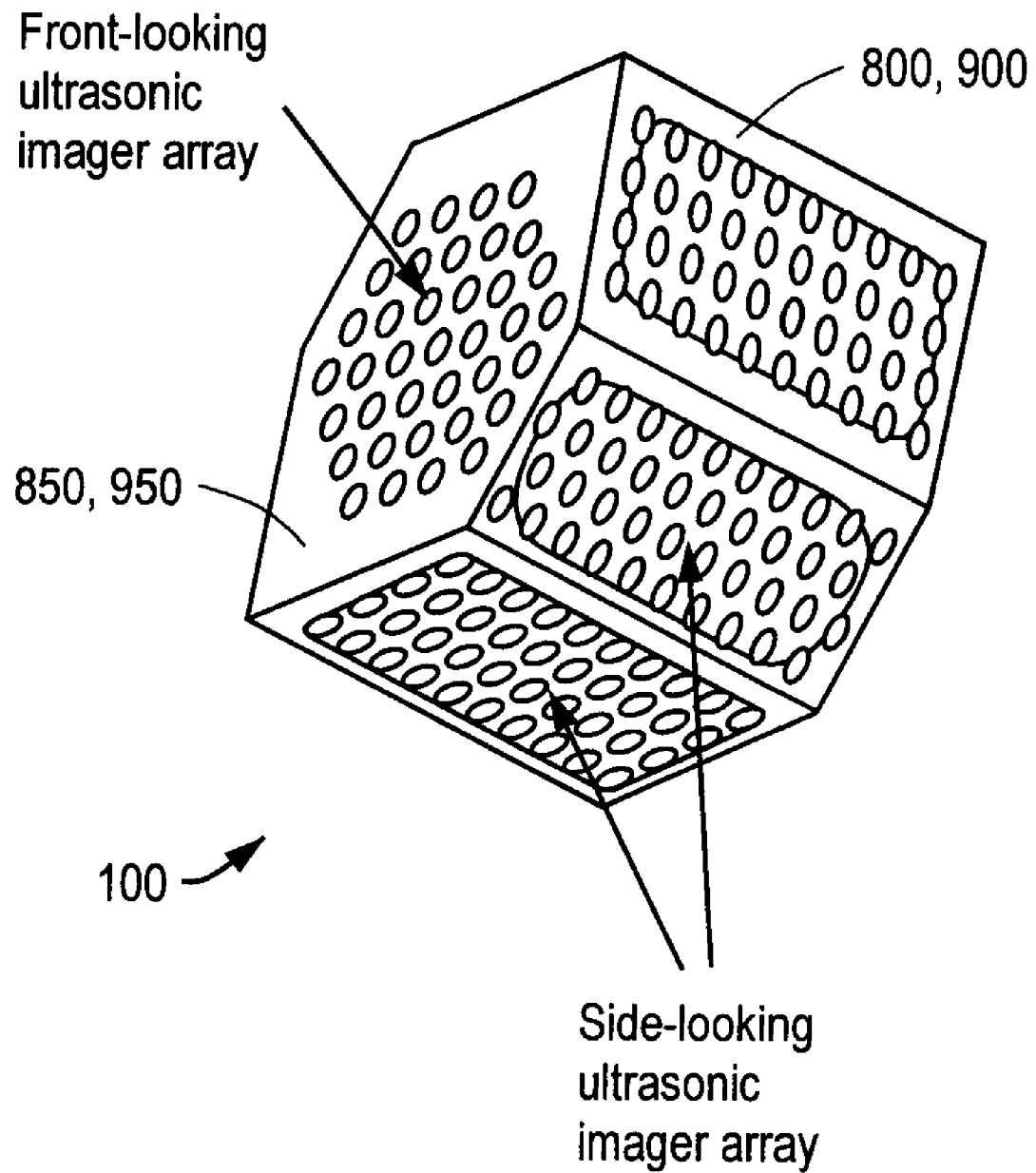
FIG. 1 illustrates a side perspective view of an exemplary monolithic, multi-directional ultrasonic transducer array in accordance with various aspects of the disclosure.
Figure 2:
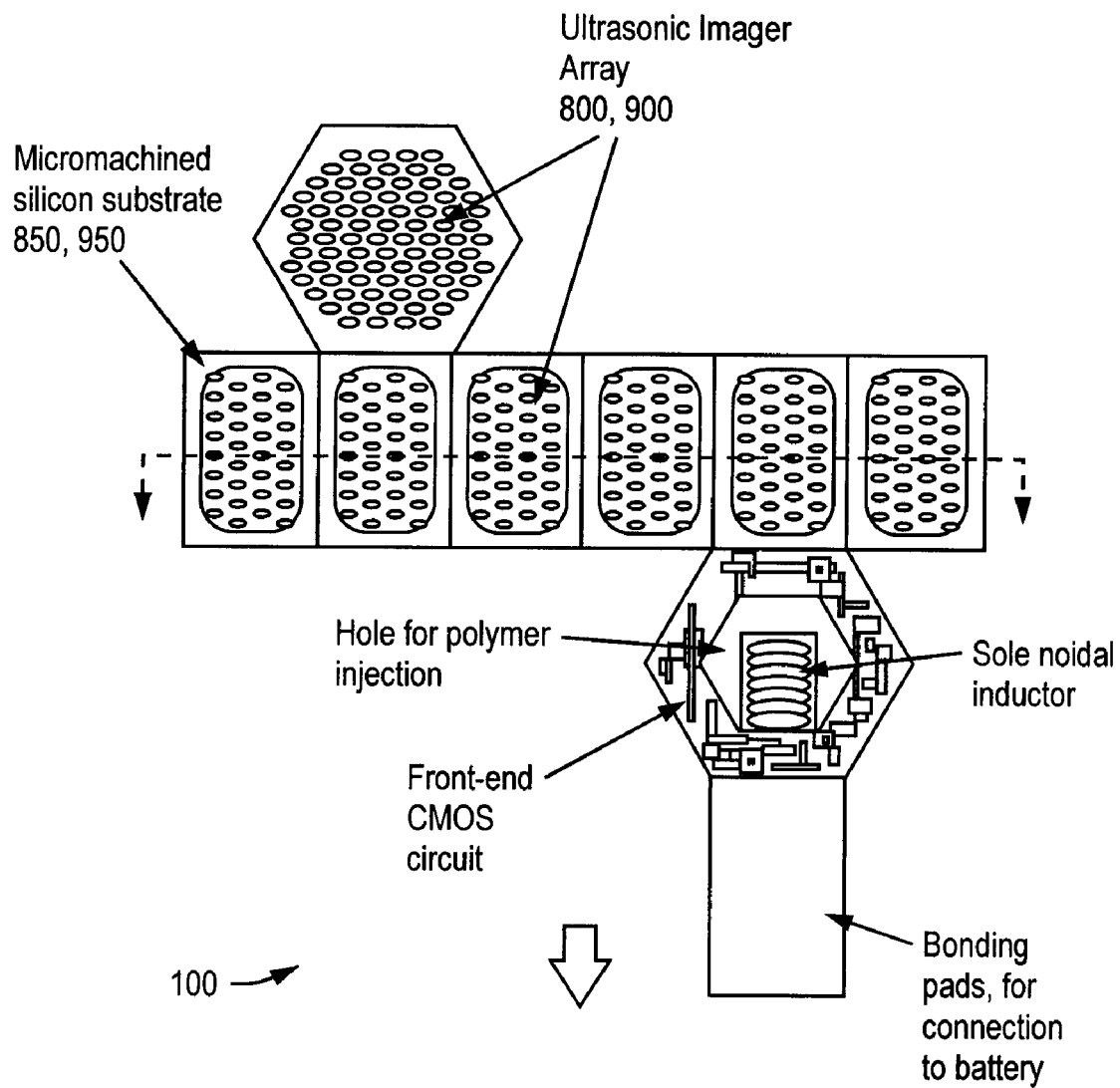
FIG. 2 is a plan view of the transducer array of FIG. 1 in an unassembled configuration.

An exemplary embodiment of a monolithic multi-directional ultrasonic transducer array 100 is illustrated in FIGS. 1 and 2. According to some aspects, the transducer array 100 may comprise an imager array. The transducer array 100 may include integrated micro-machined (e.g., MEMS) ultrasonic transducers 800, 900 and front-end CMOS signal processing circuitry 120 on one piece of silicon substrate 850, 950. As a result of the monolithic structure, a better signal-to-noise ratio and therefore better image quality may be achieved by the imager array.

Figure 3:
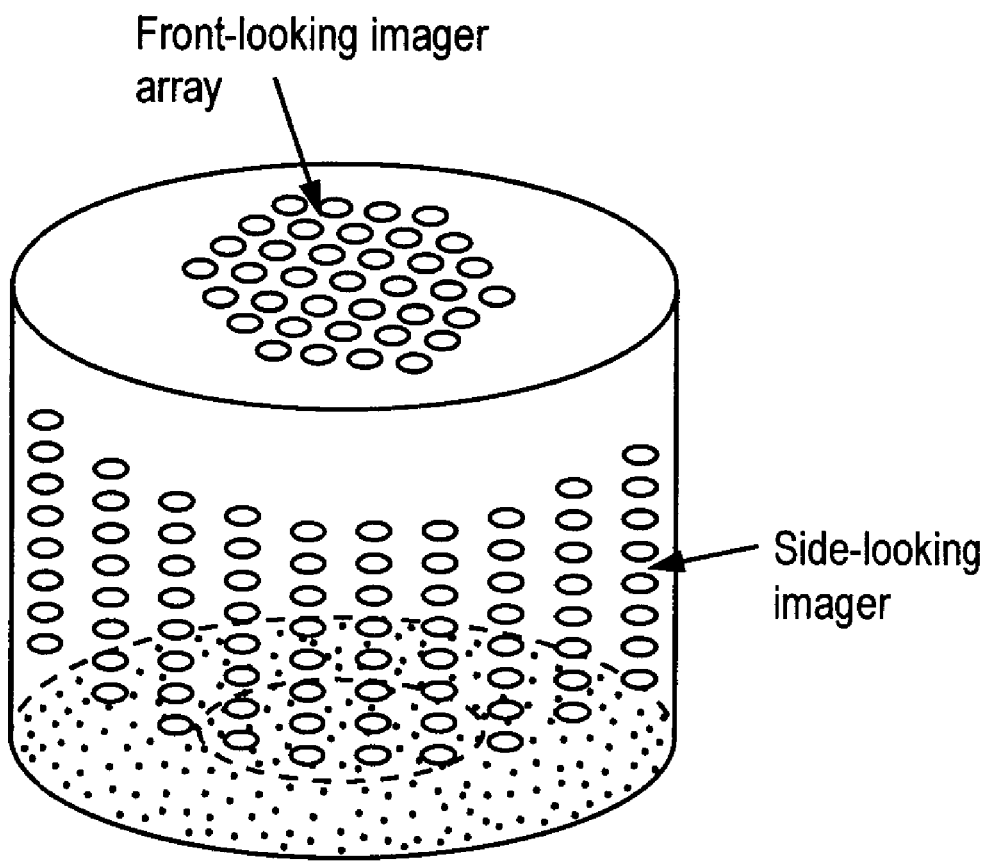
FIG. 3 illustrates a side perspective view of another exemplary monolithic, multi-directional ultrasonic transducer array in accordance with various aspects of the disclosure.

The exemplary monolithic ultrasonic imager array 100 may be divided into pieces of ultrasound-elements/CMOS-circuitry plates between which thin (1-20 μm thick) flexible silicon membranes are used for interconnection. These small plates, each typically measuring, for example, 0.8 millimeter×0.8 millimeter (for a 20 MHz ultrasonic imager) and 40 μm-100 μm thick, can be folded into a three-dimensional prism structure as shown in FIG. 1. The thin flexible silicon membranes may not only provide the physical connection for device plates but also support the thin-film electrical interconnects between the imager devices and the front-end CMOS circuitry. This 3-D ultrasonic imager array can look at multiple directions as needed for many medical applications including capsule endoscope and intravascular diagnosis. Although in FIGS. 1 and 2 a hexagonal prism is illustrated, this technology is capable of constructing multi-direction looking ultrasonic cameras of any prism shape or a cylindrical shape, as shown in FIG. 3.

Figure 4:
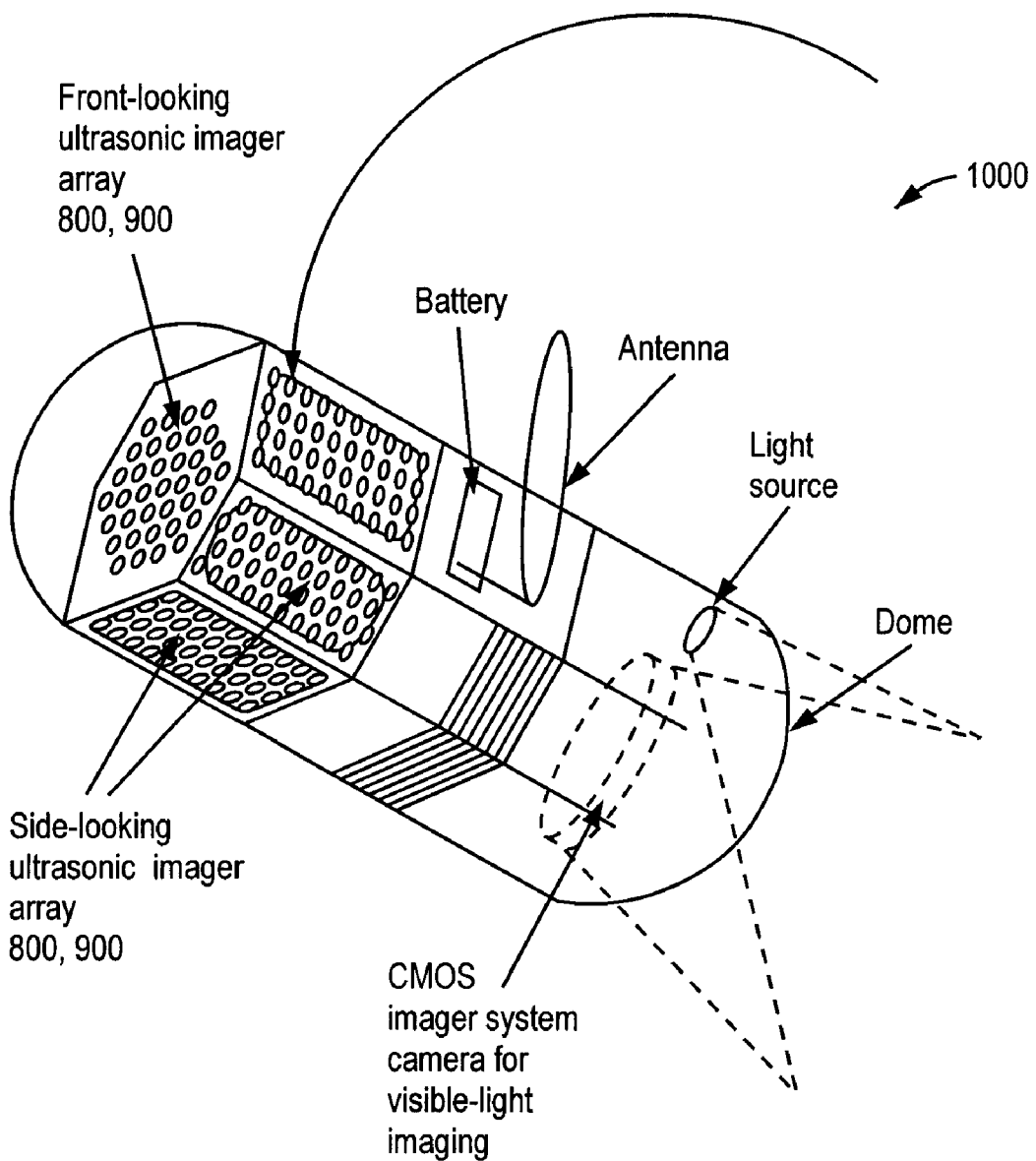
FIG. 4 is a side perspective view of an exemplary wireless, multi-directional ultrasonic capsule endoscope in accordance with various aspects of the disclosure.

Referring now to FIG. 4, an ultrasonic capsule camera 1000 is illustrated. On the capsule camera 1000, each ultrasonic imager comprises a two-dimensional ultrasonic transducer array. The capacitive ultrasonic transducer element is able to generate ultrasonic waves upon application of an a.c. electrical signal on its membrane. The same membrane may also work as an ultrasonic sensor, which will deform and generate an electrical signal upon reception of impinging ultrasonic waves.

After being assembled, miniature fixing platforms made of micromachined silicon may be used to fix the ultrasonic imager in its prism or cylindrical shape, and silicone or other bio-compatible polymers may be used to fill into the cavity inside the prism so the whole structure will be glued together. The polymer may also provide the mechanical support for this pill camera so it would not crush easily by external pressure. The diameter of this ultrasonic camera pill typically ranges from 0.4 millimeters (for 50 MHZ ultrasounds) to 1.6 millimeters (for 10 MHz ultrasounds), while its length is about 2 millimeters. A MEMS spiral inductor antenna may be integrated with this pill structure either monolithically or flip-chip bonded on the silicon substrate for sending out the image signals. This multi-direction-looking ultrasonic camera may be complementary to an optical imager capsule endoscope (i.e., Pillcam) and can provide additional diagnostic information not available from a regular optical camera capsule endoscope. This exemplary ultrasonic imaging pill may be integrated with a CMOS imager, such that this minimally invasive capsule is capable of shooting ultrasound images in addition to color photographs from inside the digestive organs The exemplary ultrasonic capsule camera is able to look at multiple directions simultaneously when traveling through the digestive tract. Additionally, ultrasound can penetrate through the tissue and provide in-depth images of tumors or any abnormity of the digestive organs. This capability may be useful for diagnosing the early stage of cancer tumors and other tissue disorders. On this platform, ultrasound transducers of different resonant frequency can be integrated on one imager for different depth detection/imaging. Due to the penetration capability, this ultrasonic imaging capsule is capable of grabbing images of the colon or rectum when it travels inside them. This could potentially provide an alternative for colonoscopy, which is an expensive diagnostic process and generally causes much discomfort for the patient.

In addition to capsule endoscopy, this multi-direction-looking ultrasonic device may be useful for intravascular ultrasonic (IVUS) imaging. Most of the commercial IVUS heads are made by assembling piezoelectric ultrasound transducers that are bulky and difficult to integrate with signal processing circuitry. For example, the commercial IVUS heads are typically 0.5-4 millimeter in diameter. In contrast, the MEMS monolithic imaging head described in this invention disclosure is about 3-4 times smaller in diameter than commercial piezoelectric IVUS tools and are suitable for reaching inside fine vessels. The MEMS ultrasonic transducer devices on this imaging system are made of thin-film drum structures. Drums of different diameter (which corresponds to the target frequency of the ultrasound) can be monolithically integrated on one silicon substrate to emit and sense ultrasounds of different wavelength. As a result, one more advantage of using the exemplary MEMS ultrasonic imager device of this disclosure is that the front-looking imagers can be designed independently of the side-looking imagers in their imaging wavelength/frequency. For conventional ceramic materials, it is hard to do so since a single piece of piezoelectric element is cut, and the inter-element spacing must be identical. Allowing front-looking and side-looking imager elements to "see" at different wavelengths will eliminate many limitations associated with the current IVUS and open new applications in cardiovascular diagnosis. Additionally, all of the conventional IVUS use a one-dimensional ultrasonic transducer array for side looking, and they provide only two-dimensional images perpendicular to the orientation of the blood vessel. The MEMS ultrasonic transducer arrays of this disclosure integrate a two-dimensional array along the catheter sidewall direction and are uniquely the first IVUS heads capable of real-time three-dimensional images for side viewing. Thus, the transducer arrays of this disclosure can provide diagnostic information not available from any conventional IVUS.

On this ultrasonic capsule camera, each ultrasonic imager comprises a two-dimensional ultrasonic transducer array 800, 900. The capacitive ultrasonic transducer element is able to generate ultrasonic waves upon application of an a.c. electrical signal on its membrane. The same membrane may also work as an ultrasonic sensor, which will deform and generate an electrical signal upon reception of impinging ultrasonic waves.

The endoscope may be similar to the Micro-Electro-Mechanical System (MEMS) implantable ultrasonic imager array, described for example, in U.S. provisional patent application No. 60/734,385 and U.S. patent application Ser. No. 11/320,921, the contents of both of which are incorporated herein by reference in their entirety. Different from the limited one-direction looking capability of Pillcam, the exemplary wireless multi-direction-looking ultrasonic capsule endoscope 1000 shown in FIG. 4 is able to provide front-looking and/or multi-directional side-looking capabilities simultaneously.

Figure 5A:
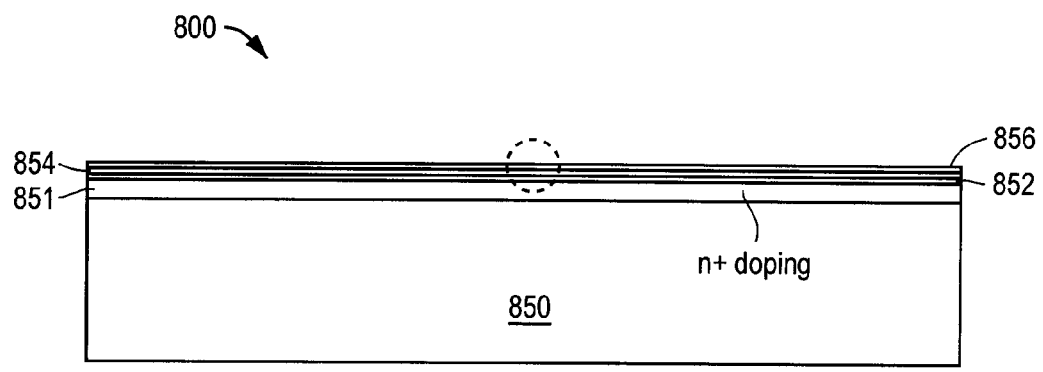
FIGS. 5A-5R are cross-sectional views of an exemplary transducer illustrating an exemplary process in accordance with aspects of the invention.
Figure 5B:
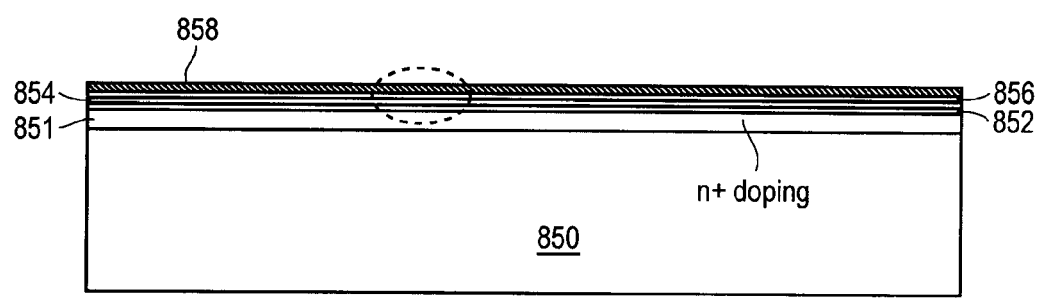
Figure 5C:
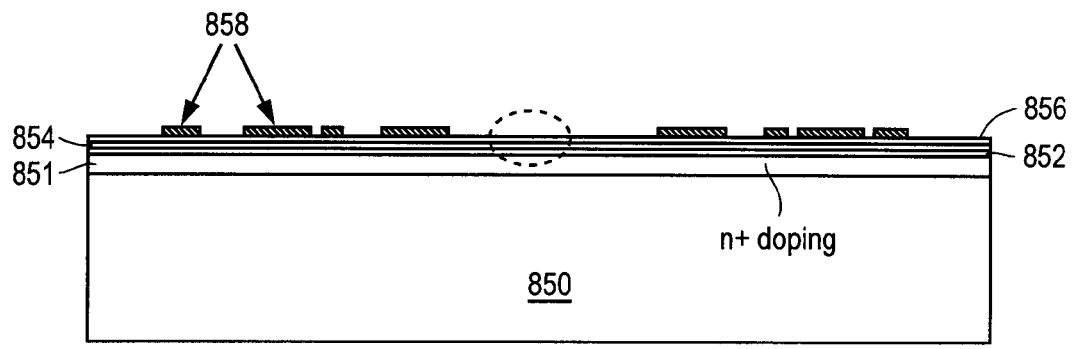
Figure 5D:
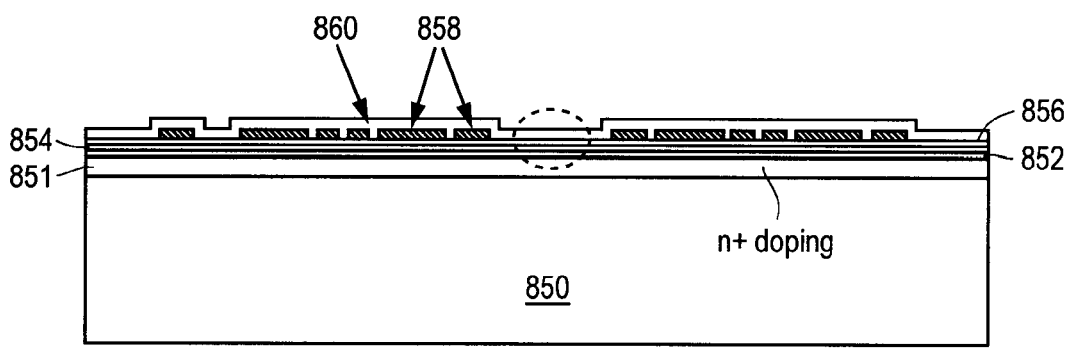
Figure 5E:
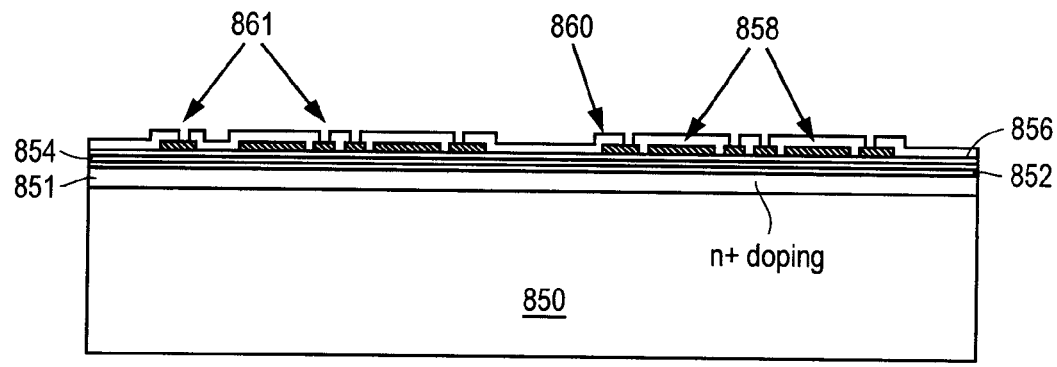
Figure 5F:
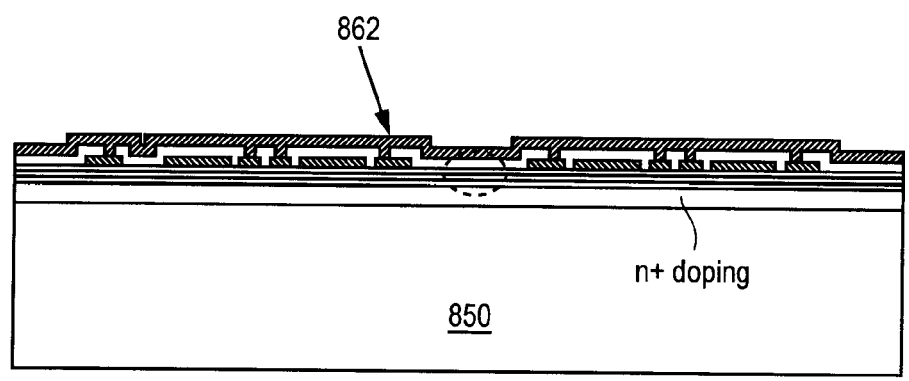
Figure 5G:
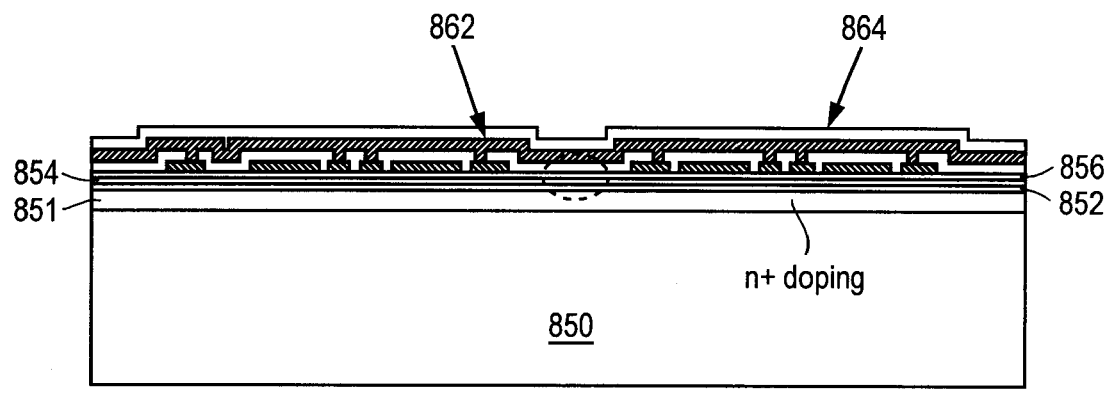
Figure 5H:
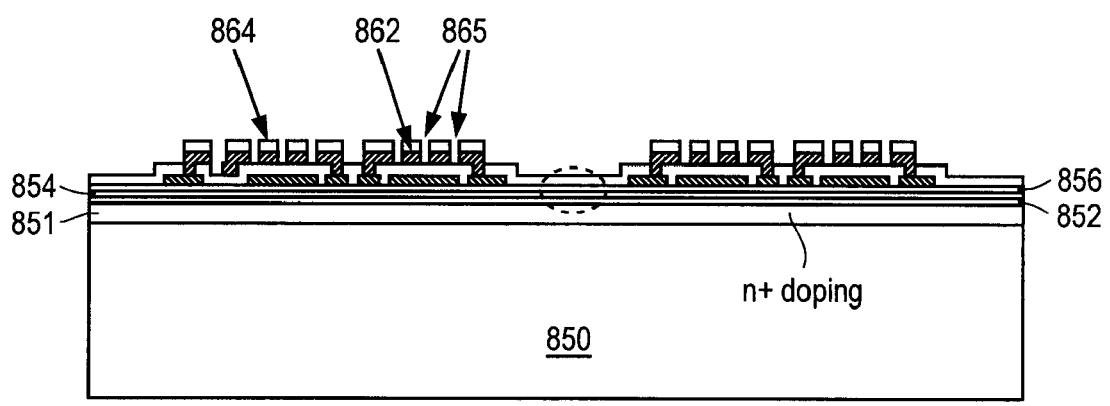
Figure 5I:
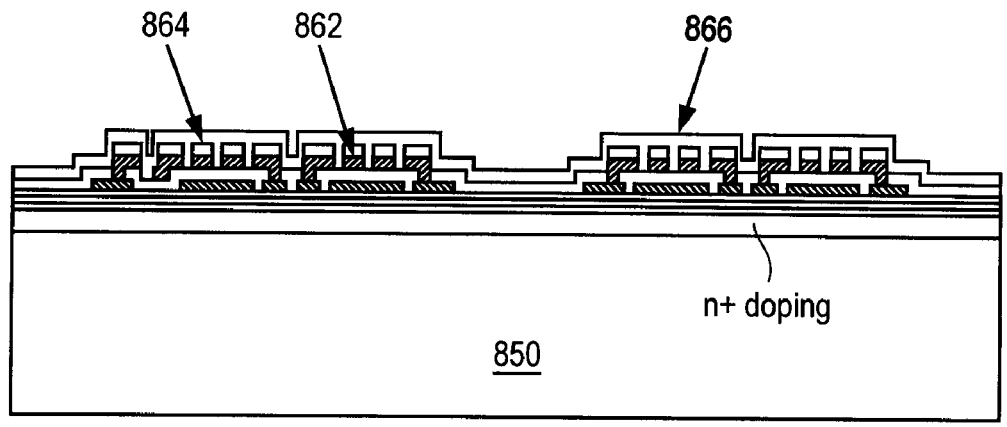
Figure 5J:
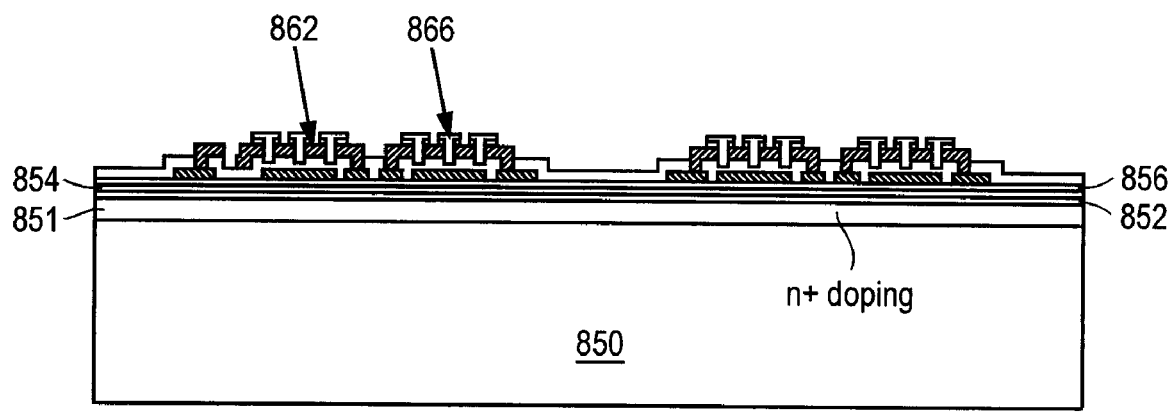
Figure 5K:
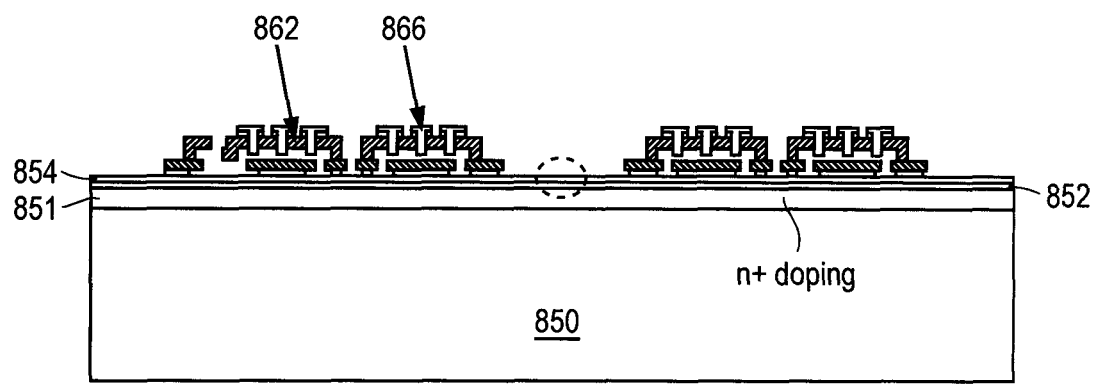
Figure 5L:
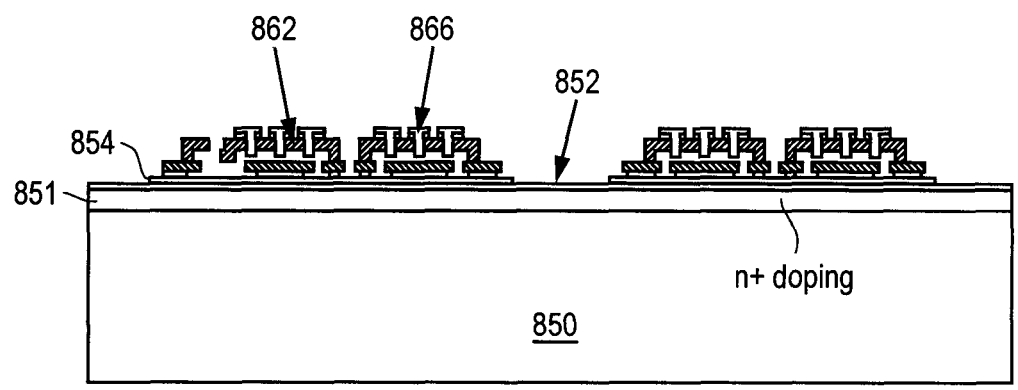
Figure 5M:
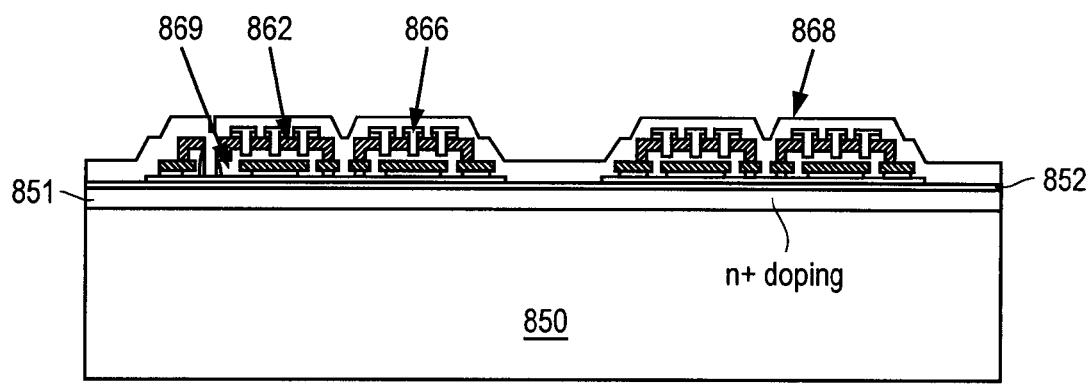
Figure 5N:
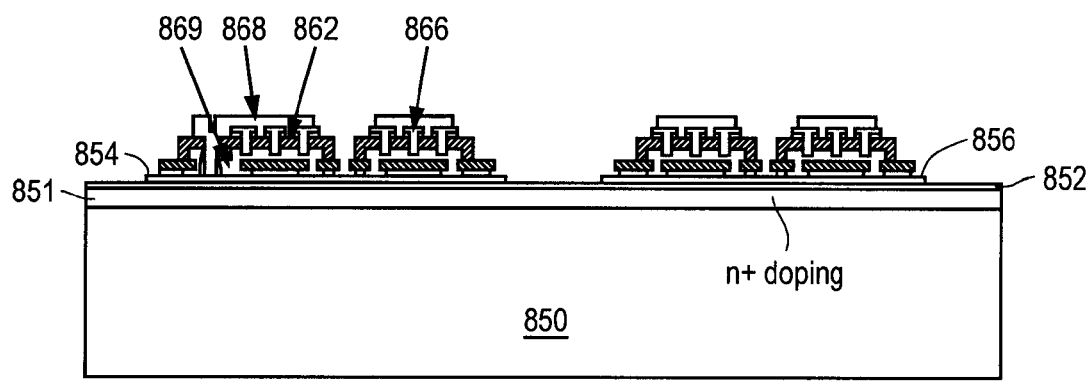
Figure 5O:
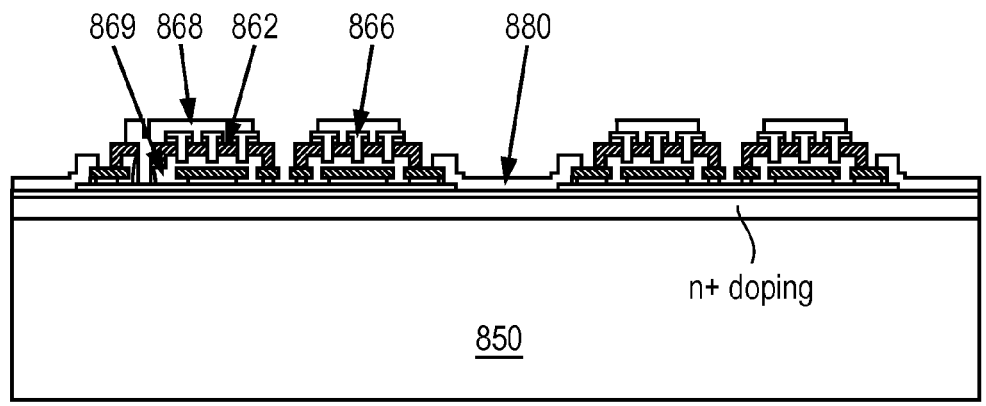
Figure 5P:
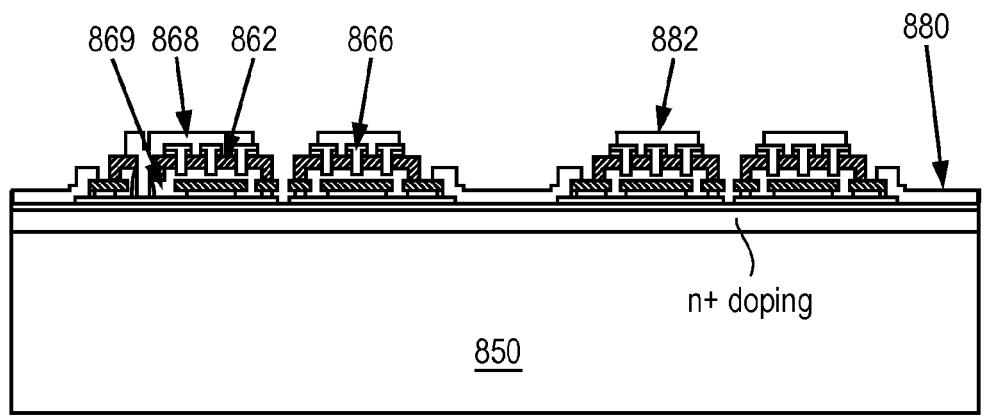
Figure 5Q:
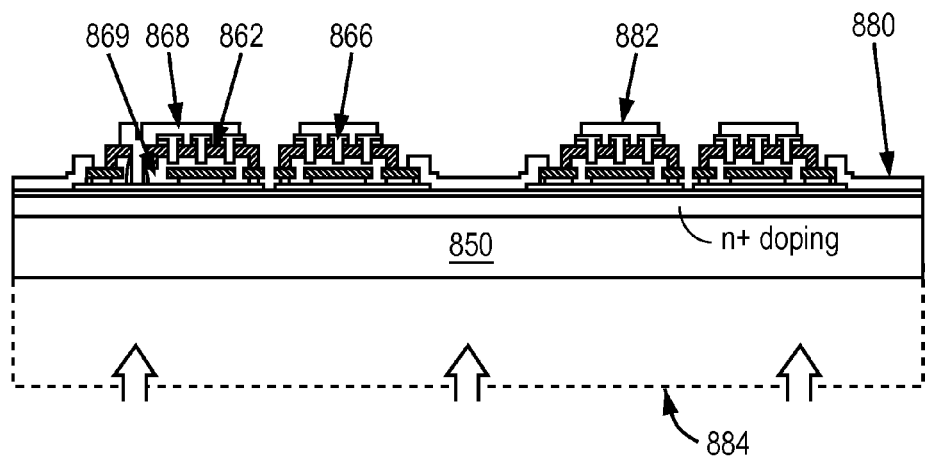
Figure 5R:
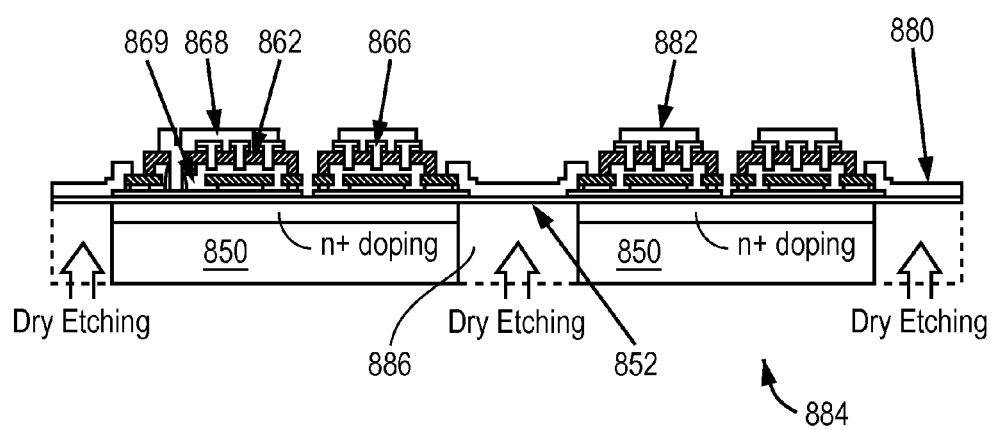

Referring now to FIGS. 5A-5R, an exemplary process of making an exemplary transducer 800 will be described. As shown in FIG. 5A, the surface of the silicon substrate 850 may be doped using, for example, diffusion or ion implantation to create a highly conducting surface layer 851. This layer 851 may reduce or prevent charge feedthrough to the substrate 850 from the electrostatic devices on the surface.

After the doping process, the layer of thermal oxide 852 may be grown on the surface of the substrate 850 and serve as a first dielectric layer. Two additional dielectric layers, for example, the silicon nitride layer 854 and the silicon dioxide layer 856 may then be deposited on top of the thermal oxide layer 852 using, for example, low pressure chemical vapor deposition (LPCVD) or other known chemical vapor deposition (CVD) processes.

Referring now to FIG. 5B, on top of the sandwiched dielectric layers (e.g., silicon dioxide/silicon nitride/silicon dioxide), the semiconductor layer 858 comprising, for example, polysilicon or other conducting thin film, may be deposited, doped, and annealed to reduce the residual stress. The semiconductor layer 858 may work as a counter electrode for the drum membrane as well as for the electrical interconnects.

As shown in FIG. 5C, a photolithography process may be used to define patterns of the semiconductor layer 858. A dry etching, for example, hydrogen fluoride (HF) etching, may be used to remove the exposed portion (not covered by a masking photoresist) of the semiconductor layer 858, thus transferring the patterns into the semiconductor layer 858. The process may then proceed to step described in relation to FIG. 5D. However, in an alternative embodiment (not shown), with the masking photoresist still on, another dry etching, for example, HF etching, may be used to remove the exposed top dielectric layer 856 comprising, for example, silicon dioxide. Thus, the second dielectric layer 854 comprising, for example, silicon nitride, may be exposed everywhere except where the semiconductor layer 858 is still present. The top dielectric layer 856 is thus self-aligned with the semiconductor layer 858 comprising, for example, a polysilicon structure. With this arrangement, the semiconductor layer 858 may be anchored to the substrate 850 through the third dielectric layer 856, which may comprise a silicon dioxide film instead of silicon nitride. However, the remainder of the substrate 850 is covered by the second dielectric layer 854, which may comprise, for example, silicon nitride, that survives from HF etching in the subsequent HF release etching process.

Referring to FIG. 5D, a thin layer of a sacrificial oxide 860 may be deposited next. The thickness of this sacrificial oxide 860 determines the gap height between the membrane and its counter electrode. As shown in FIG. 5E, the sacrificial oxide may be patterned using a photolithography process and a dry etching such as, for example, HF etching, to form dimples (not shown) and anchoring holes.

Turning now to FIG. 5F, a second semiconductor layer 862 comprising, for example, structural polysilicon, may be deposited, doped, and annealed. As shown in FIG. 5G, a thin layer 864 of silicon dioxide may be deposited, for example, via LPCVD. The thin layer 864 of silicon dioxide may be about 500 angstroms thick.

Next, as shown in FIG. 5H, the thin layer of silicon dioxide 864 and the second semiconductor layer 862 may be patterned to form a membrane using a photolithography process and a dry etching such as, for example, HF etching. The etching process may etch through the second semiconductor layer and overetch into the sacrificial oxide 860 to form pits 865 into the sacrificial oxide. The pits may be about 300-500 angstroms deep.

Referring now to FIG. 5I, a layer 866 of silicon nitride may be deposited, for example, via LPCVD. The thin layer 864 of silicon dioxide vertically separates the second semiconductor layer 862 from the layer 866 of silicon nitride. The layer 866 of silicon nitride may be about 0.3 μm and may fill the dimple pits in the sacrificial oxide 860. The typical area of the pits is 2 μm×2 μm, and the thin film layer 866 of silicon nitride may not be able to fill the pits completely. A hollow-core nitride column may thus be formed.

As shown in FIG. 5J, the thin layer of silicon nitride film 866 may be patterned via a photolithography process and a dry etching such as, for example, HF etching. Then, as shown in FIG. 5K, conventional dry or wet etching may be used to remove the sacrificial oxide 860 and the top dielectric layer 856 (if not removed in the step shown in FIG. 5C) to release microstructures of the second semiconductor layer 862 from the substrate 850. This dry/wet etching may also undercut the thin oxide layer under the first semiconductor layer 858. Due to the etch rate difference between the sacrificial oxide and the high-quality LPCVD oxide under the first semiconductor layer 858, the length of the undercut is small and will not degrade the anchoring robustness of the first semiconductor layer 858.

Turning to FIG. 5L, a photolithography step and a dry etching may be used to remove regions of the layer 854 of silicon nitride over which metal interconnects will meander. Removal of these regions of the silicon nitride layer 854 reduces the contact area between the metal lines and the nitride film 854 in order to minimize charging problems.

Referring now to FIG. 5M, a thick layer of PECVD or other deposited oxide 868, for example, tetraethoxysilane (TEOS), may be used to seal the release holes. As these thin-film deposition processes are performed in vacuum, the cavity 869 under the semiconductor membrane 862 may be sealed under vacuum. A photolithography process and a dry and/or wet etch may be used to pattern the sealing oxide 868 such that the oxide thickness is reduced to about 4000 angstroms on most of the device areas except areas around the release holes and in the center of the membrane, as shown in FIG. 5N. The oxide left on the center of the membrane may be used to improve the frequency response of the membrane.

Referring now to FIG. 5O, a metal layer may be deposited and patterned to form metal interconnects 880. Turning to FIG. 5P, a polymer passivation dielectric layer 882 may be deposited and patterned. The passivation layer may include a layer of PECVD oxide and/or a relatively thick (e.g., several microns) layer of parylene C.

As shown in FIG. 5Q, conventional dry or wet etching from the backside 884 may be used to thin the silicon substrate 850, for example, to approximately 80-140 μm thick. Turning to FIG. 5R, a photolithography step and a dry etching from the backside 884 may be used to form deep trenches 886 in the substrate. The transducer array 800 resulting from the process illustrated via FIGS. 9A-9R may be used is a variety of medical devices, as discussed in more detail below.

Figure 6A:
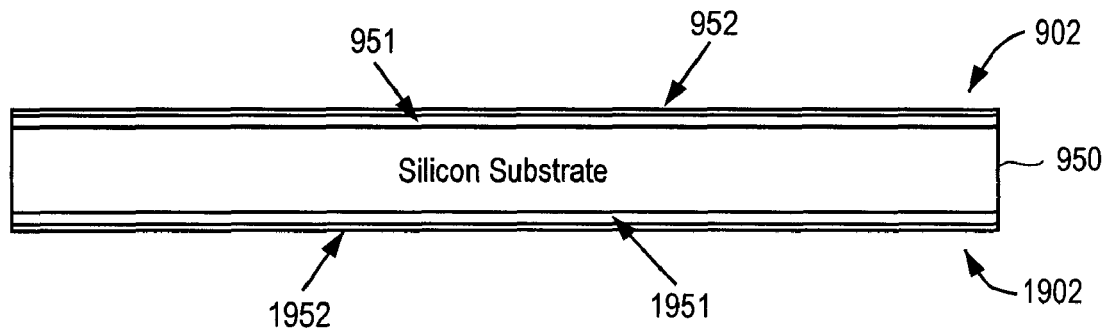
FIGS. 6A-6BB are cross-sectional views of an exemplary transducer illustrating an exemplary process in accordance with aspects of the invention.
Figure 6B:
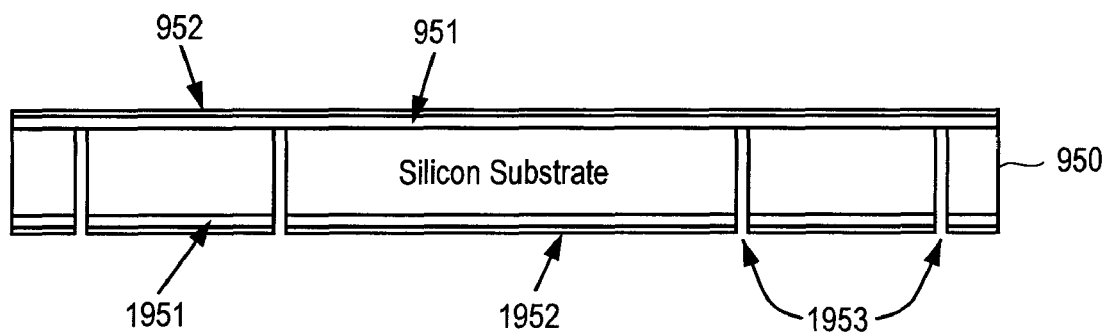
Figure 6C:
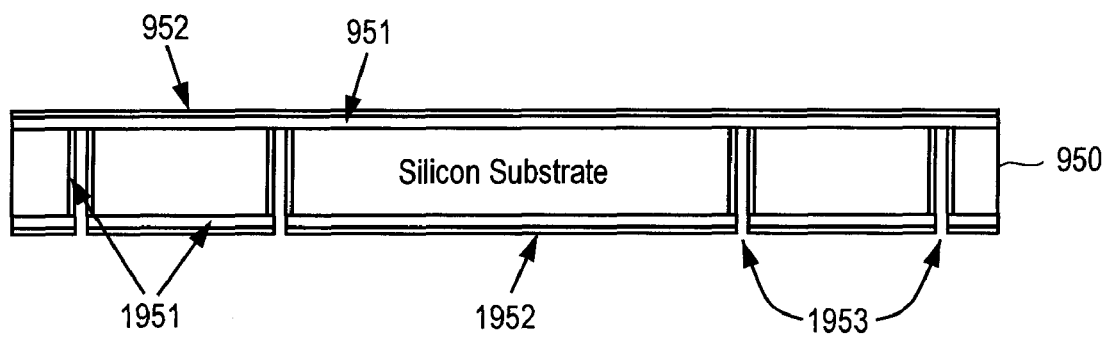
Figure 6E:
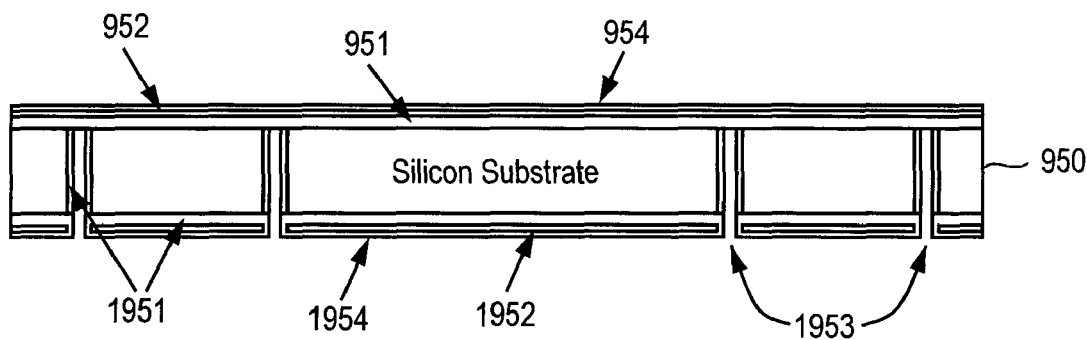
Figure 6E:
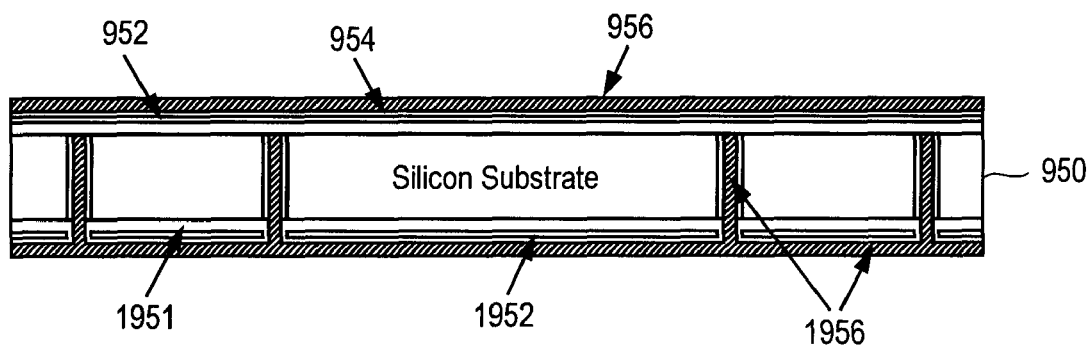
Figure 6F:
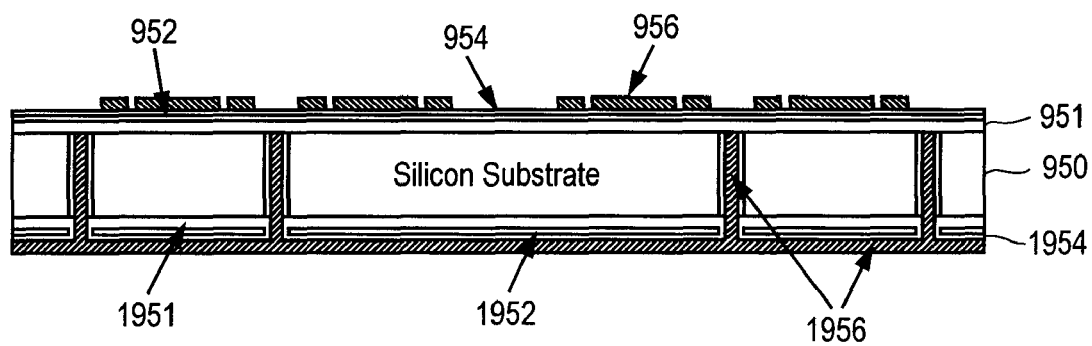
Figure 6G:
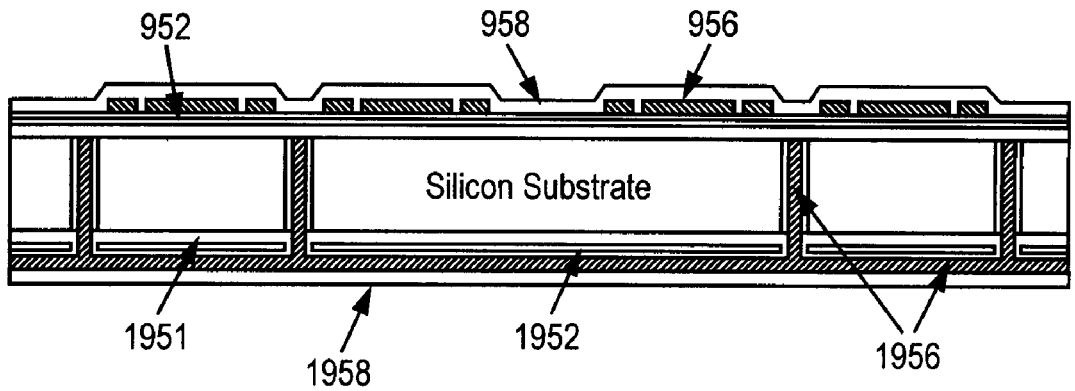
Figure 6H:
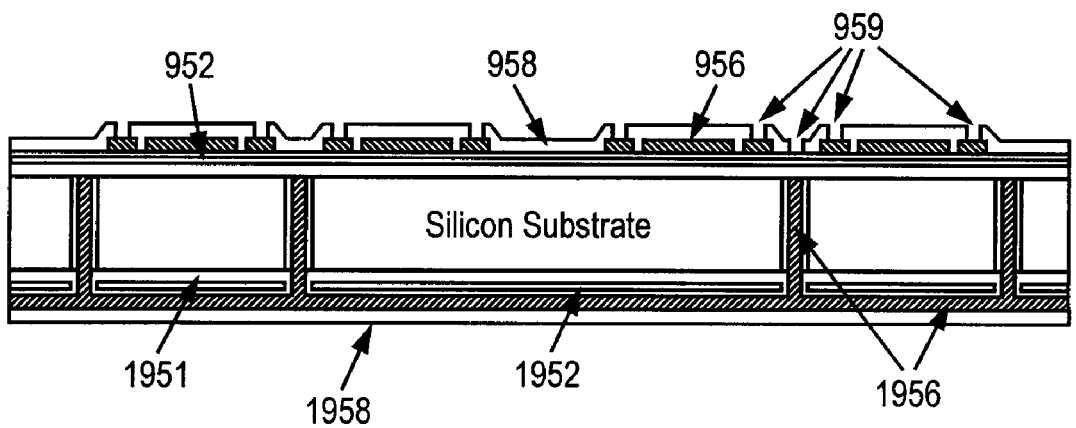
Figure 6I:
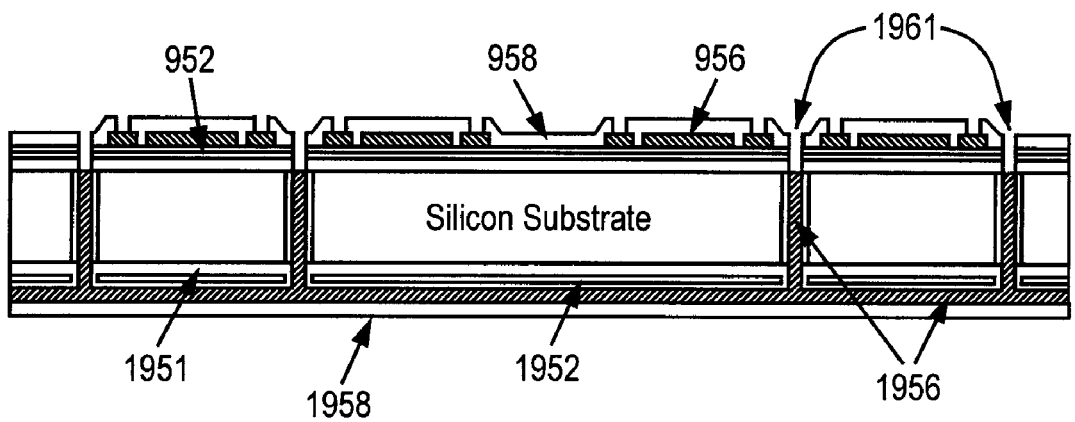
Figure 6M:
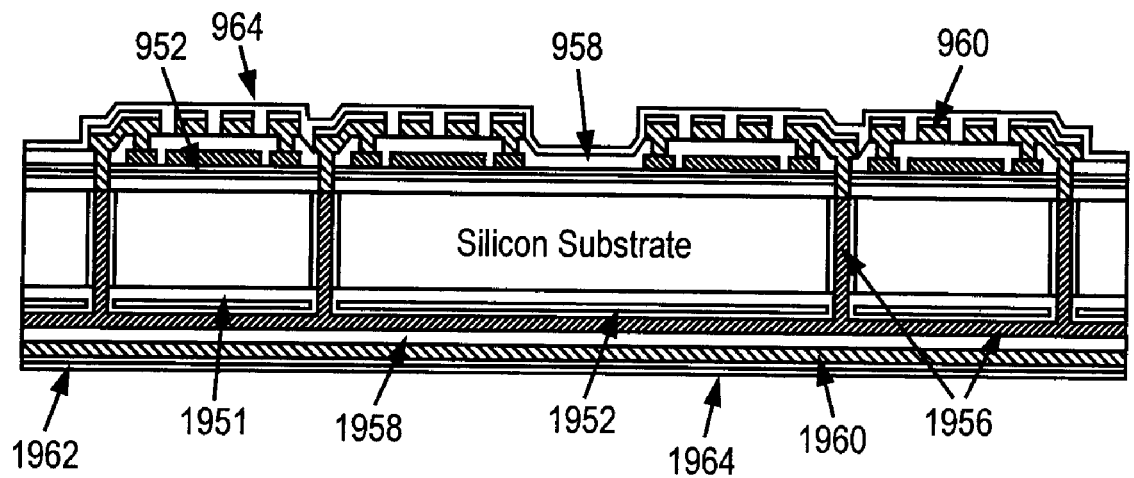
Figure 6N:
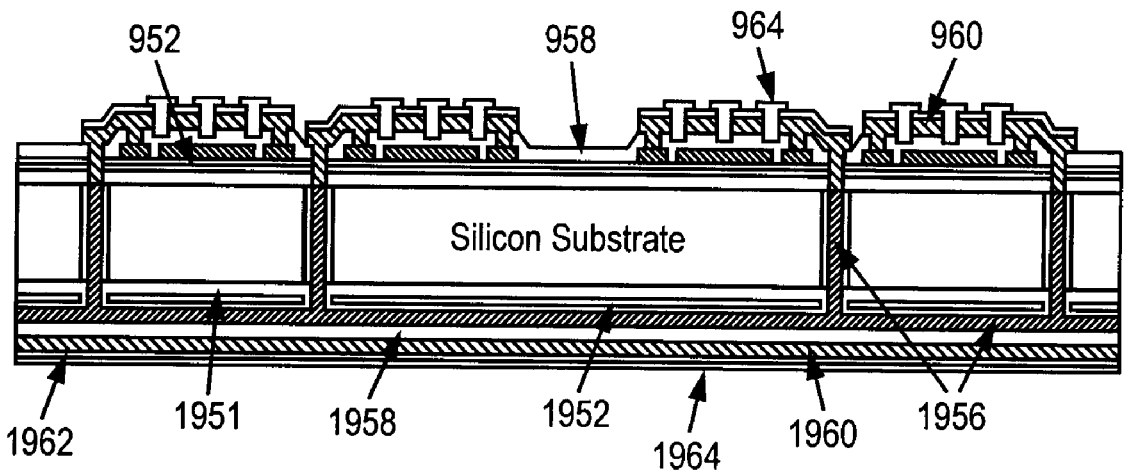
Figure 6O:
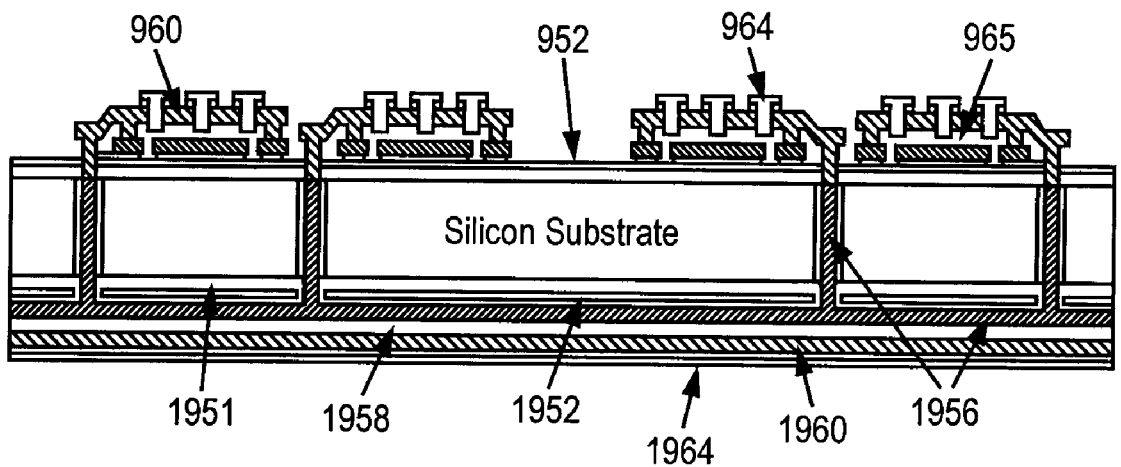
Figure 6J:
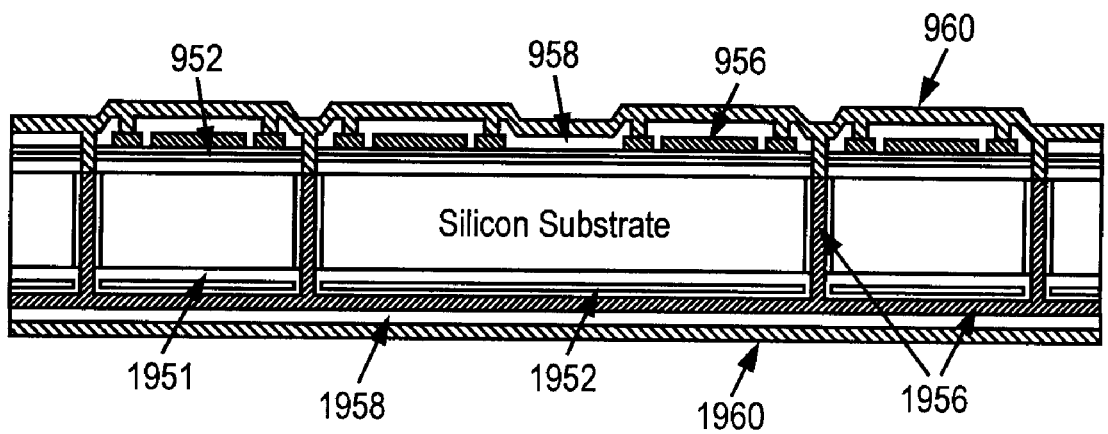
Figure 6K:
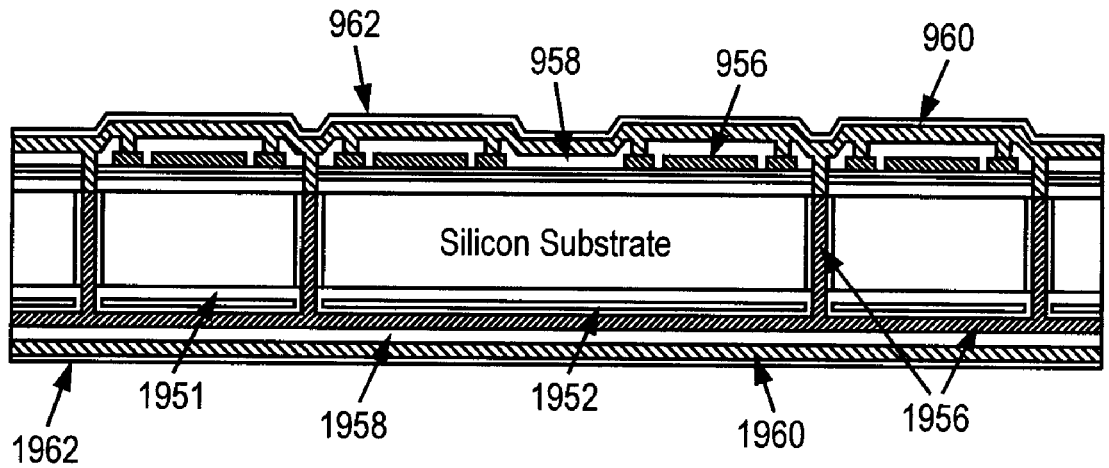
Figure 6L:
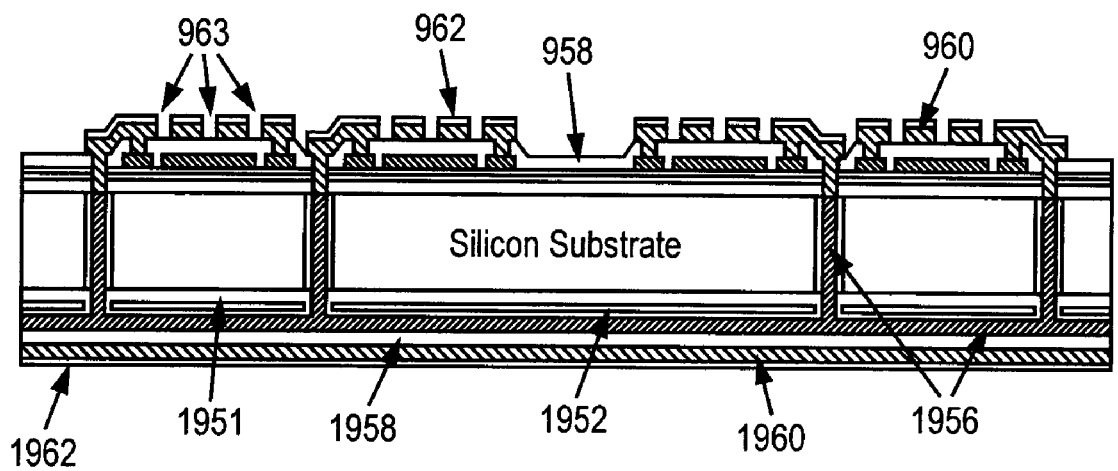
Figure 6P:
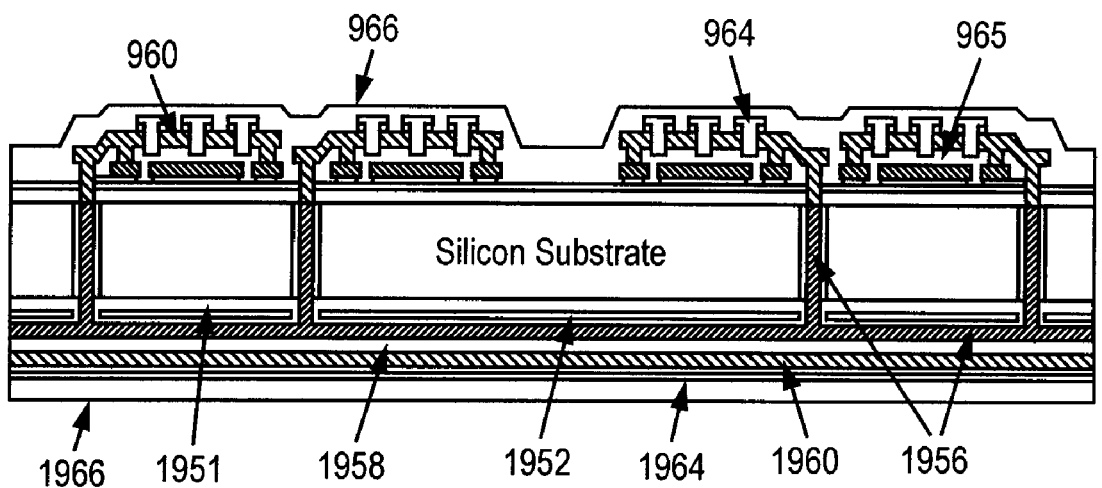
Figure 6Q:
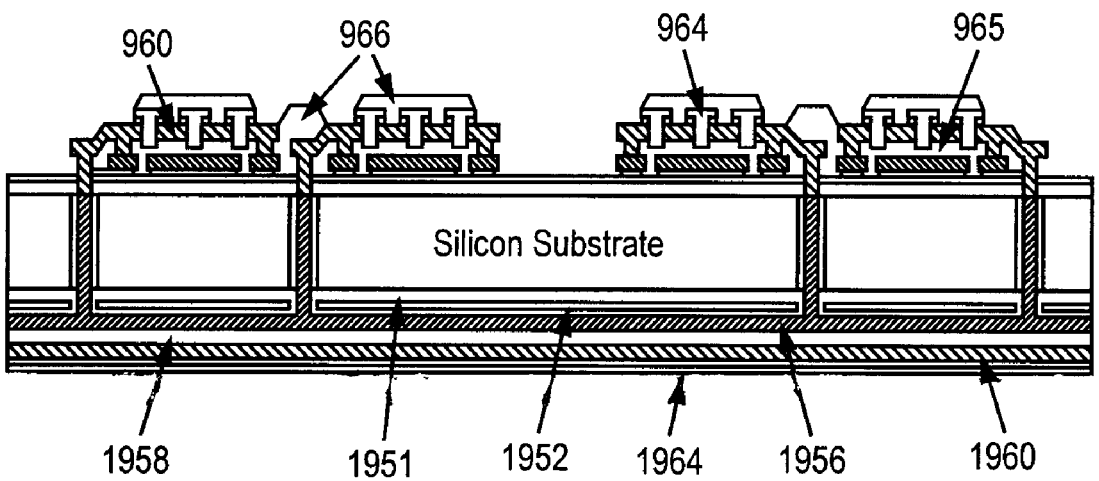
Figure 6R:
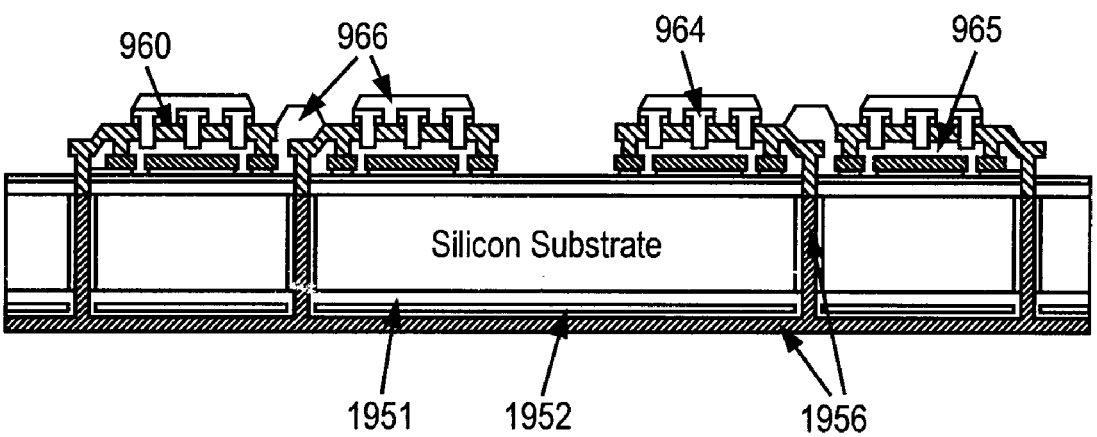
Figure 6S:
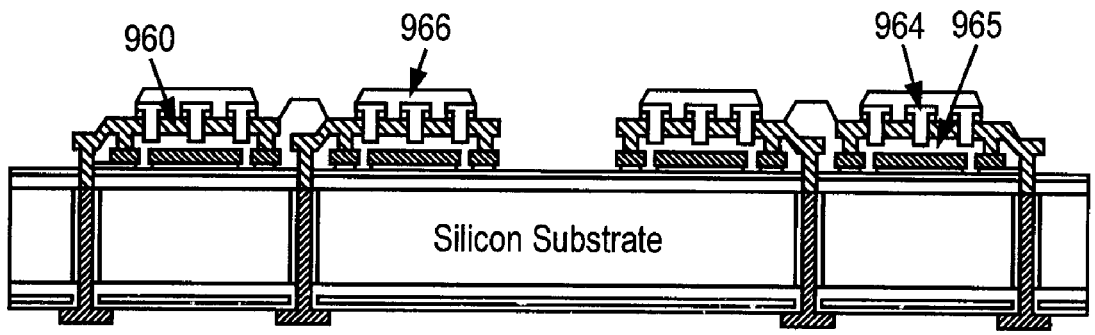
Figure 6T:
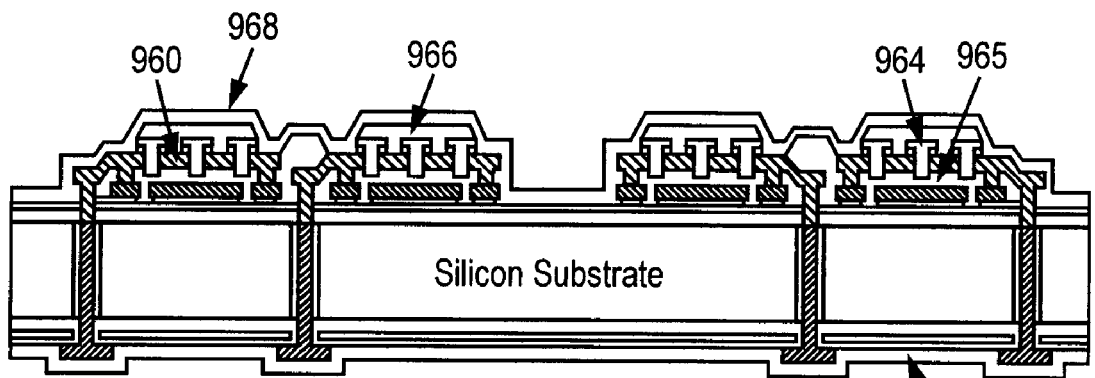
Figure 6U:
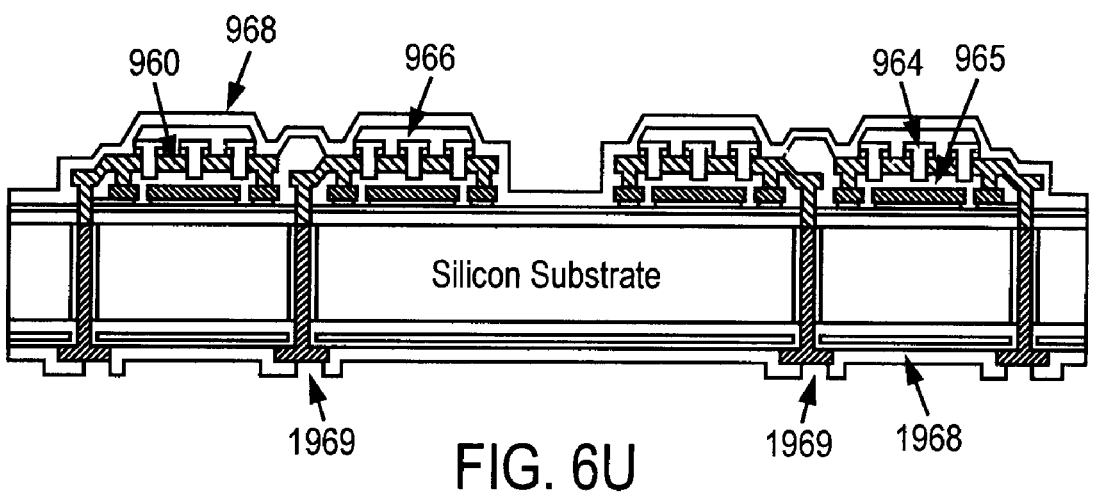
Figure 6V:
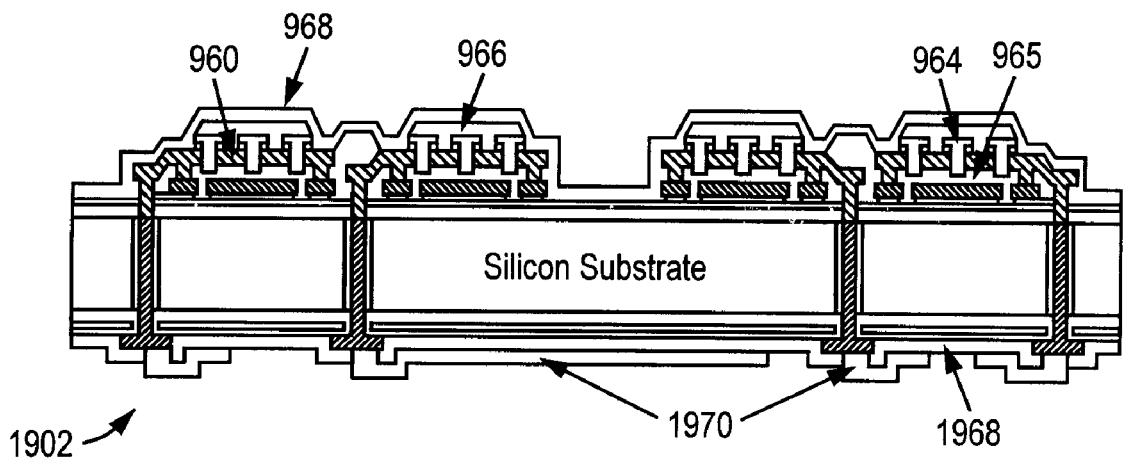
Figure 6W:
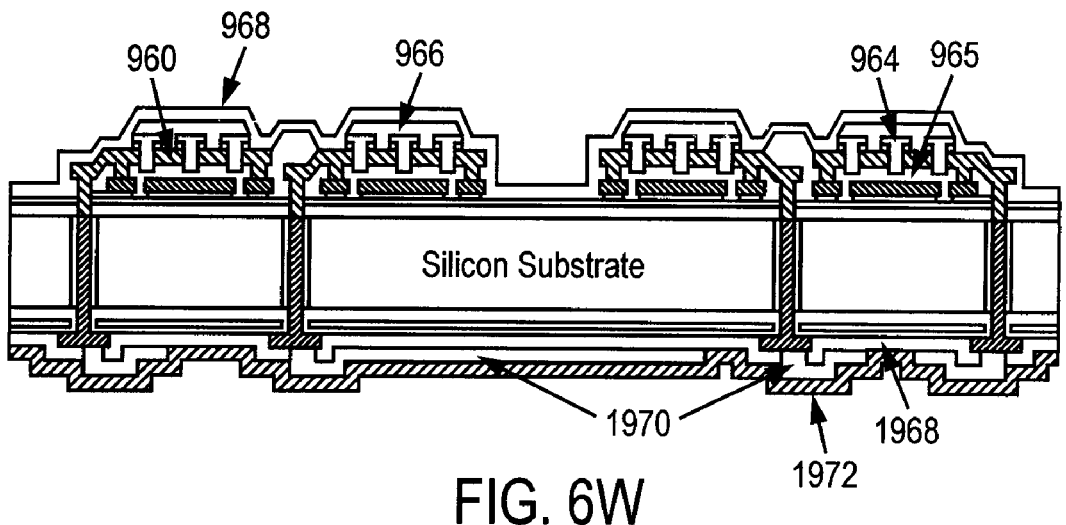
Figure 6X:
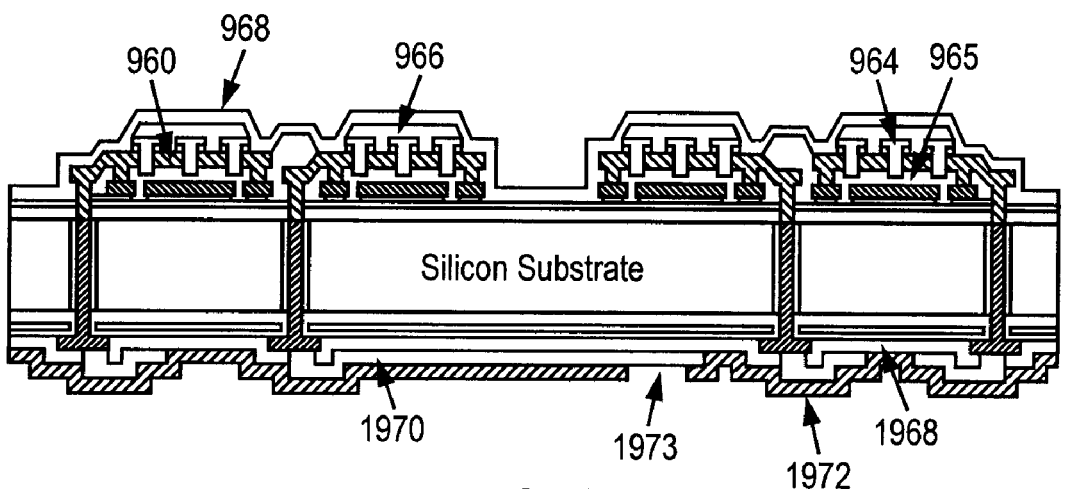
Figure 6Y:
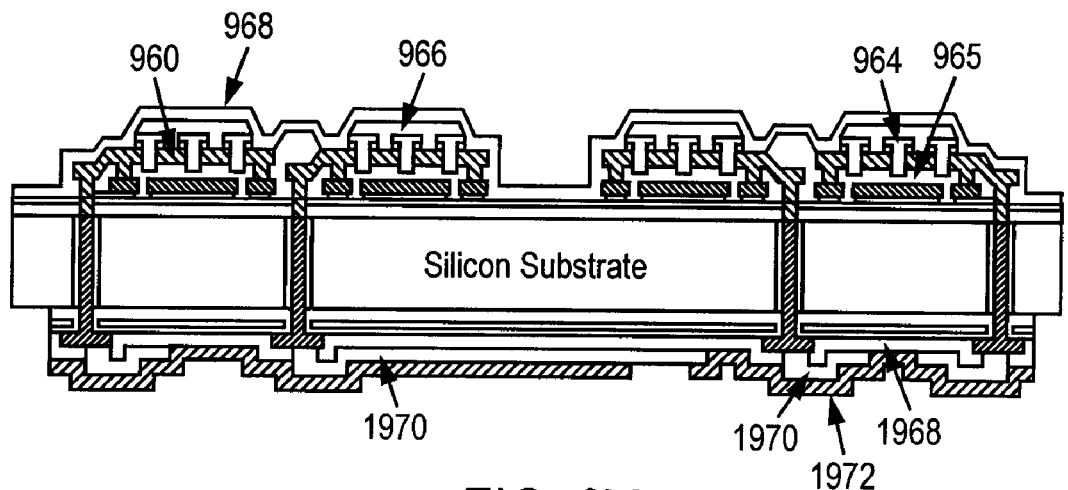
Figure 6Z:
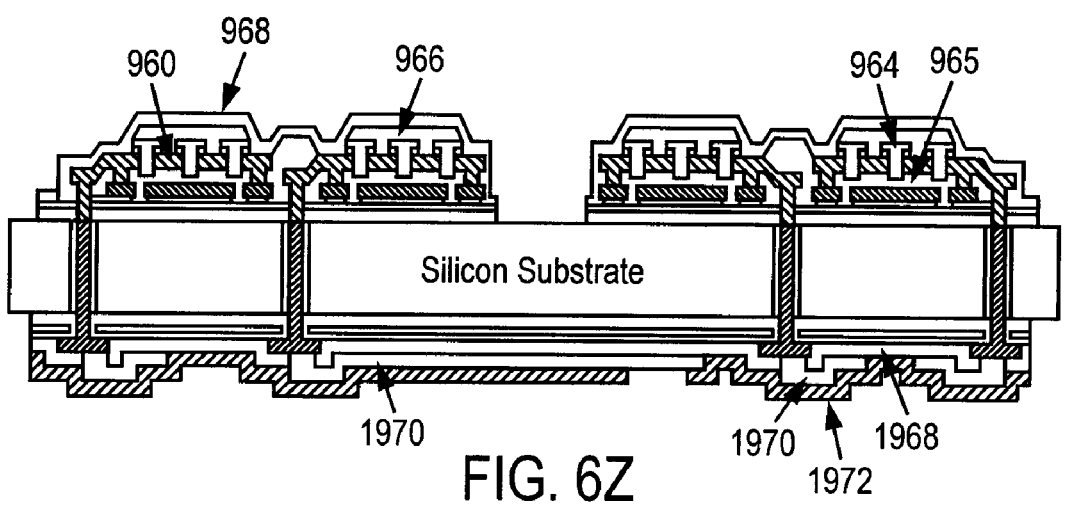
Figure 6A:
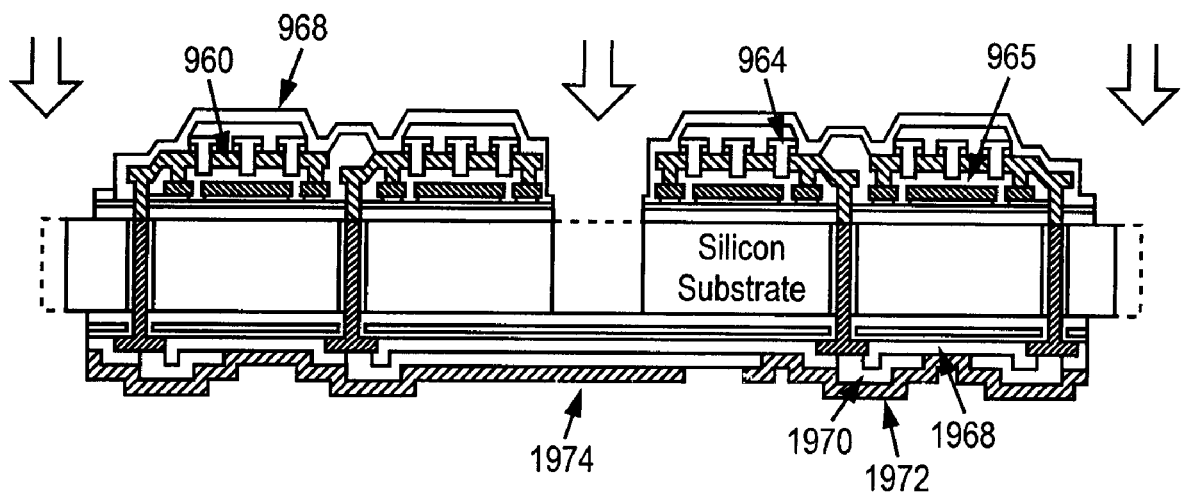
Figure 6B:
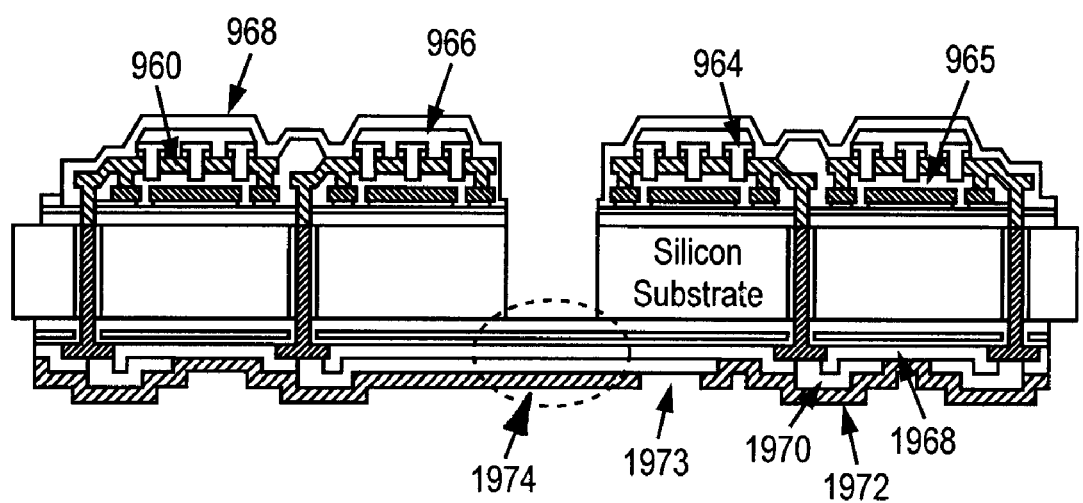

Referring now to FIGS. 6A-6Z, an exemplary process of making an exemplary transducer 900 will be described. The fabrication of this monolithic three-dimensional ultrasonic array 900 starts with a thick silicon wafer approximately 100 μm thick. As shown in FIG. 6A, layers of silicon dioxide 951, 1951 may be grown thermally on both surfaces 902, 1902 of the substrate 950 and serve as a first dielectric layer. The layers 951, 1951 of silicon dioxide may be relatively thick at about 1.0 μm. Dielectric layers, for example, silicon nitride layers 952, 1952 may then be deposited on top of the thermal oxide layers 951, 1951 using, for example, low pressure chemical vapor deposition (LPCVD) or other known chemical vapor deposition (CVD) processes. These nitride layers are used to anchor the micro-structures to the silicon substrate during the HF sacrificial etching process. The silicon nitride layers 952, 1952 may be approximately 2000 angstroms thick.

Referring now to FIG. 6B, a photolithography process and a reactive ion etching are next used to pattern the backside of the substrate, exposing the holes for through-wafer channels. A deep silicon dry etching is then used to create an array of through-wafer channels 1953. The dimensions of the channel openings may be, for example, 4 μm×4 μm. As shown in FIG. 6C, thermal oxidation is next used to convert the surface of the channel wall from silicon into silicon dioxide. Thus, the sidewall of the through-wafer channels is covered with a layer of silicon dioxide 1951. This oxide layer is used to insulate the substrate from the conductor that is to be filled in the channel in the subsequent step.

Turning to FIG. 6D, a thin (approx. 250-300 angstroms) layer of silicon dioxide 954, 1954 is then deposited on both sides of the substrate via LPCVD deposition. This thin silicon dioxide layer covers the silicon nitride layer. This oxide layer is used to separate the doped polysilicon (to be deposited next) from the silicon nitride for reducing charging problems associated with silicon nitride film.

A layer of in-situ doped polysilicon 956, 1956 is next deposited on both sides of the substrate using LPCVD, as shown in FIG. 6E. This polysilicon paves the surface of the substrate and forms a continuous conduction channel from the backside of the wafer to the front end of the channel. Next, as illustrated in FIG. 6F, the polysilicon on the front-side of the wafer is next patterned to form the polysilicon electrodes and anchoring structures. The patterning may be achieved, for example, via photolithography and a reactive ion etching.

Referring now to FIG. 6G, a layer of CVD oxide 958, 1958 is next deposited. This layer of CVD oxide 958, 1958 serves as a sacrificial layer. A photolithography and a reactive ion etching are then used to open anchor holes 959 in this sacrificial oxide, as shown in FIG. 6H. As illustrated in FIG. 6I, another photolithography and a dry etching are next used to open via holes 961 over the through-wafer channels. The via holes 961 cut through multiple layers of oxide and nitride and expose the polysilicon in the through-wafer channel.

Turning to FIG. 6J, a layer of polysilicon 960, 1960 is deposited via LPCVD deposition and doped. This polysilicon fills in the via-holes to form a continuous conduction path through the through-wafer channel to the backside polysilicon. It also works as the structural polysilicon for constructing the transducer membrane and other microstructures.

Next, as shown in FIG. 6K, a thin (200-300 angstroms) layer 962, 1962 of oxide, for example, silicon dioxide, is deposited using LPCVD. This oxide is used to separate the doped polysilicon from a silicon nitride that is to be deposited subsequently. A photolithography and a reactive ion etching are then used to pattern the thin buffer oxide and the structural polysilicon using one mask, as illustrated in FIG. 6L. This patterning process defines the geometrical shape of the transducer membrane and excavates an array of holes 963 inside the membrane which will be used to form the dielectric posts. In this dry etching process, after the exposed polysilicon is completely etched away, an intentional over-etch is used to create an array of 200-300 angstroms deep pits on the sacrificial oxide. These pits are to be used as molds to form dielectric posts which protrude from the lower surface of the polysilicon membrane after a subsequent nitride deposition. The function of the posts is to prevent shorting of the polysilicon membrane to its counter electrode.

Referring now to FIG. 6M, a layer of LPCVD silicon nitride 964, 1964 is next deposited to fill in the post holes as well as coat the rest of the wafer surface. As shown in FIG. 6N, the wafer is then patterned using a photolithography process on the front side. Only the silicon nitride film covering the post holes or around their vicinity is reserved. The rest is etched away using, for example, reactive ion etching. This etching step also partially etches the thin oxide layer under the silicon nitride.

The next step is the removal of sacrificial oxide 958 to free the polysilicon microstructures, as illustrated in FIG. 6O. The sacrificial oxide 958 may be etched away using either a wet or dry etching. In this release etching process, the thin oxide 954 under the polysilicon 956 is partially undercut forming cavities 965, which may be sealed under vacuum. However, due to the very thin oxide used in this kind of sandwiched (nitride/thinoxide/polysilicon) structure and the slow etch rate of the high-quality LPCVD oxide (compared with the fast etch rate of sacrificial oxide), the extent of undercut is limited to an acceptable range and will not degrade the mechanical strength of the anchors of the microstructures to the substrate.

Turning to FIG. 6P, a sealing oxide 966, 1966, typically TEOS deposited by PECVD or LPCVD, is next deposited to seal the release holes. This sealing oxide is patterned using photolithography and a dry and/or wet etching, as shown in FIG. 6Q. The sealing oxide is stripped from the backside using wet or dry etching.

Referring to FIG. 6R, with the front-side of the wafer protected by a layer of photoresist, another dry or wet etching is used to remove the silicon nitride 1964, the silicon dioxide 1962, the polysilicon 1960, and the sacrificial oxide 1958 from the backside. A photolithography process and a dry etching, for example, reactive ion etching, are then used to pattern the polysilicon on the backside, as shown in FIG. 6S. Both sides of the wafer are next coated with a layer of polymer 968, 1968, as illustrated by FIG. 6T. As shown in FIG. 6U, the polymer on the backside is patterned to expose the via holes 1969 on which metal interconnects will connect to the polysilicon underneath. The patterning may be achieved, for example, by photolithography and reactive ion etching.

Turning now to FIG. 6V, a thin layer of metal 1970 is next deposited and patterned as electrical interconnects on the backside. Another layer of polymer 1972 is then deposited on the backside 1902 to passivate the metal interconnects, as shown in FIG. 6W. This polymer film is patterned, for example, by photolithography and reactive ion etching, to expose the metal on the bonding pad areas 1973 on the backside, as illustrated in FIG. 6X.

Referring now to FIG. 6Y, a photolithography process and a dry etching, for example, reactive ion etching, are next used to pattern the backside dielectrics (FIG. 28). This step exposes the silicon substrate over a uniform band area surrounding the device boundary. This is the first masking step to define the boundary for individual devices. Another photolithography process and a dry etching are next used to pattern the dielectrics on the front side, as shown in FIG. 6Z. This step exposes the silicon substrate on areas for inter-imager-plate connection as well as the boundary of the device. This is the second masking step to define the boundary for individual device separation.

With the same masking photoresist used for the processing step described in connection with FIG. 6Z, a deep silicon etching is used to cut through the wafer. As illustrated in FIG. 6AA, this etching step releases the imager array from the substrate. Referring to FIG. 6BB, this etching step also forms a flexible dielectric inter-plate connection 1974 between imager plates by removing the substrate silicon on the connection region. The imager array can then be assembled into a three dimensional imaging device as shown in FIGS. 1-4.

Referring now to FIG. 7, an exemplary medical device 1000 may comprise one of the aforementioned transducer arrays. The exemplary medical device 1000 may work both as an emitter to generate ultrasounds and a sensor to detect ultrasounds. When the device 1000 works as an emitter, the transducer 818 is driven by an ac electrical signal applied between the membrane 862 and the counter electrode 860. The ac electrical signal may produce a time varying electrostatic force on the membrane 862 that urges the membrane 862 to move up and down. This movement generates mechanical waves which transmit out to the media surrounding the membrane 862. During this electrostatic actuation process, electrical charges are periodically received into and removed from the variable capacitor, which is defined by the membrane 862 and the counter electrode 860.

It will be apparent to those skilled in the art that various modifications and variations can be made in the medical devices and methods of the present invention without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A method of fabricating an array of ultrasonic transducers for a medical imaging device, the method comprising:
   forming an array of ultrasonic transducer elements such that forming each transducer element includes
      doping a surface of a substrate to create a highly conducting surface layer;
      forming a plurality of sandwiched dielectric layers including
         growing a layer of thermal oxide on the highly conducting surface layer of said substrate;
         depositing a layer of silicon nitride on said layer of thermal oxide;
         depositing a layer of silicon dioxide on said layer of silicon nitride, said layers of silicon dioxide and thermal oxide sandwiching said layer of silicon nitride such that said layer of silicon nitride is in direct contact with said layer of thermal oxide and said layer of silicon dioxide;
      forming a first layer of semiconductor thin film on said dielectric layers, said first layer of semiconductor thin film and said substrate sandwiching said plurality of dielectric layers;
      forming a second layer of semiconductor thin film having a portion in contact with said first layer of semiconductor thin film and a portion separated from said first layer of semiconductor thin film, said second layer having at least on hold therethrough such that said first layer of semiconductor thin film and said substrate sandwiching said plurality of dielectric layers, and said second layer of semiconductor thin film are disposed directly about said doped surface;
      forming a vacuum cavity between said first and second layers of semiconductor thin film, said first and second layers of semiconductor thin film comprising opposing walls of said vacuum cavity; and
      forming a silicon nitride film on said second layer of semiconductor thin film, said silicon nitride film extending through said hole in the second layer and into said vacuum cavity so as to prevent portions of the second layer from collapsing said vacuum cavity and contacting said first layer of the array of ultrasonic transducer elements.

2. The method of claim 1, wherein said layer of thermal oxide comprises a layer of silicon dioxide.

3. The method of claim 1, wherein said first layer of semiconductor thin film or said second layer of semiconductor thin film comprises a layer of polysilicon.

4. The method of claim 2, further comprising doping said polysilicon layer.

5. The method of claim 1, further comprising creating patterns in said first layer of semiconductor thin film the associated with at least two transducer elements of said array.

6. The method of claim 5, further comprising electrically connecting said two elements of the array.

7. The method of claim 6, said connecting comprising connecting the two elements to one another by a metal interconnect.

8. The method of claim 1, wherein the method includes:
forming another array of ultrasonic transducer elements couples to said array of ultrasonic transducer elements; and
performing said coupling by forming a flexible dielectric inter-plate connection such that said array and said other array are arranged as part of a three-dimensional structure.

9. The method of claim 8, wherein the method includes arranging said array and said other array as part of a hexagonal structure with said array and said other array on different side of said hexagonal structure.

10. The method of claim 8, wherein the method includes arranging said array and said other array as part of a cylindrical structure with said flexible dielectric inter-plate connection curved between said array and said other array.

11. A medical imaging device comprising:
an array of ultrasonic transducer elements, each transducer element comprising
a substrate having a doped surface creating a highly conducting surface layer;
a plurality of sandwiched dielectric layers including
a layer of thermal oxide on said substrate;
a layer of silicon nitride on said layer of thermal oxide;
a layer of silicon dioxide on said layer of silicon nitride, said layers of silicon dioxide and thermal oxide sandwiching said layer of silicon nitride such that said layer of silicon nitride is in direct contact with said layer of thermal oxide and said layer of silicon dioxide;
a first layer of semiconductor thin film on said dielectric layers, said first layer of semiconductor thin film and said substrate sandwiching said plurality of dielectric layers;
a second layer of semiconductor thin film having a portion in contact with said first layer of semiconductor thin film and a portion separated from said first layer of semiconductor thin film, said second layer having at least one hole therethrough such that said first layer of semiconductor thin film and said substrate sandwiching said plurality of dielectric layers, and said second layer of semiconductor thin film are disposed directly about said doped surface;
a vacuum cavity between said first and second layers of semiconductor thin film, and first and second layers of semiconductor thin film comprising opposing walls of said vacuum cavity; and
a silicon nitride film on said second layer of semiconductor thin film, said silicon nitride film extending through said hole in the second layer and into said vacuum cavity so as to prevent portions of said second layer from collapsing said vacuum cavity and contacting said first layer of the array of ultrasonic transducer elements.

12. The medical imaging device of claim 11, further comprising an oxide layer sandwiched between said silicon nitride film and said second layer.

13. The medical imaging device of claim 12, wherein said oxide layer substantially limits contact between said silicon nitride film and said second layer to sidewalls of said at least one hole.

14. The medical imaging device of claim 11, wherein said medical device comprises a wireless capsule endoscope.

15. The medical imaging device of claim 11, wherein said medical imaging device comprises:
another array of ultrasonic transducer elements coupled to said array of ultrasonic transducer elements by a flexible dielectric inner-plate connection such that said array and said other array are arranged as part of a three-dimensional structure.

16. The medical imaging device of claim 15, wherein said array and said other array are arranged as part of a hexagonal structure with said array and said other array on different sides of said hexagonal structure.

17. The medical imaging device of claim 15, wherein said array and said other array are arranged as part of a cylindrical structure with said flexible dielectric inter-plate connection curved between said array and said other array.

* * * * *

UNITED STATES PATENT AND TRADEMARK OFFICE
CERTIFICATE OF CORRECTION

PATENT NO. : 8,372,680 B2  
APPLICATION NO. : 11/685199  
DATED : February 12, 2013  
INVENTOR(S) : Jingkuang Chen Page 1 of 1

It is certified that error appears in the above-identified patent and that said Letters Patent is hereby corrected as shown below:

In the Claims

In column 10, line 40, in Claim 1, delete "on hold" and insert --one hole--, therefor In column 10, line 43, in Claim 1, delete "about" and insert --above--, therefor In column 10, line 64, in Claim 5, after "film", delete "the", therefor In column 11, line 6, in Claim 8, delete "couples" and insert --coupled--, therefor In column 11, line 15, in Claim 9, delete "side" and insert --sides--, therefor In column 12, line 5, in Claim 11, delete "about" and insert --above--, therefor In column 12, line 7, in Claim 11, delete "and" and insert --said--, therefor In column 12, line 30, in Claim 15, delete "inner" and insert --inter--, therefor Signed and Sealed this  
Twenty-sixth Day of November, 2013

Margaret A. Focarino  
*Commissioner for Patents of the United States Patent and Trademark Office*